United States Patent [19]
Selawry

[11] Patent Number: 6,149,907
[45] Date of Patent: *Nov. 21, 2000

[54] TREATMENTS USING SERTOLI CELLS

[75] Inventor: Helena P. Selawry, Rileyville, Va.

[73] Assignee: Research Corporation Technologies, Inc., Tucson, Ariz.

[ * ] Notice: This patent is subject to a terminal disclaimer.

[21] Appl. No.: 09/298,015

[22] Filed: Apr. 23, 1999

Related U.S. Application Data

[60] Division of application No. 08/660,258, Jun. 7, 1996, Pat. No. 5,958,404, and a continuation-in-part of application No. 08/485,340, Jun. 7, 1995, Pat. No. 5,849,285, and a continuation-in-part of application No. 08/421,641, Apr. 13, 1995, Pat. No. 5,725,854, and a continuation-in-part of application No. 08/211,695, Apr. 13, 1994, abandoned.

[51] Int. Cl.$^7$ .......................... A01N 63/00; A01N 65/00; C12N 5/00; C12N 5/02; C12N 5/06
[52] U.S. Cl. .......................... 424/93.7; 435/325; 435/326; 435/347; 435/366; 435/363; 435/373; 435/374
[58] Field of Search .................................. 435/326, 347, 435/366, 363, 373, 374, 325; 424/93.7

[56] References Cited

PUBLICATIONS

Selawry, et al. (Nov. 1991) "Production of a Factor, or Factors, Suppressing IL–2 Production and T Cell Proliferation by Sertoli Cell–Enriched Preparations. A Potential Role for Islet Transplatation in an Immunologically Privileged Site", *Transplatation* 52 (5):846–850.

Oonk, et al. (1988) "Insulin–Like Growth Factor I (IGF–I) Receptors on Sertoli Cells from Immature Rats and Age–Dependent Testicular Binding of IGF–I and Insulin", *Molecular and Cellular Endocrinology* 55:33–43.

Whitmore III, et al. (Oct. 1985) "The Role of Germinal Epithelium and Spermatogenesis in the Priviledged Survival of Intratesticular Grafts", *The Journal of Urology* 134(4):782–786.

Hofmann, et al. (Aug. 1992), Abstract No. 92347475 "Immortalization of Germ Cells and Somatic Testicular Cells Using the SV40 Large T Antigen", *Experimental Cell Research* 201(2):417–435.

Lejeune, et al. (1993), Abstract No. 93:280614 "Enhancement of Testosterone Secretion by Normal Adult Human Leydig Cells b Co–Culture with Enriched Preparations of Normal Adult Human Sertoli Cells", *Int. J. Androl.* 16(1):27–34.

Berends, et al. (1991), Abstract No. 92:167853 "Significant Improvement of the Survival of Seminoma Cells in vitro by use of a Rat Sertoli Cell Feeder Layer and Serum–Free Medium", *J. Natl. Cancer Inst.* 83(19):1400–1403.

Carreau, et al. (1988), Abstract No. 88:227147 "Stimulation of Adult Rat Leydig Cell Aromatase Activity by a Sertoli Cell Factor", *Endocrinology* 122(3):1103–1109.

*Primary Examiner*—David M. Naff
*Assistant Examiner*—Deborah K. Ware
*Attorney, Agent, or Firm*—Scully, Scott, Murhphy & Presser

[57] ABSTRACT

A method of treating a disease is provided that results from a deficiency of a biological factor which comprises administering to a mammal Sertoli cells and also cells that produce the biological factor. A method of treating diabetes mellitus is carried out by transplanting pancreatic islet of Langerhans cells in conjunction with Sertoli cells to create an immunologically privileged site. A method of creating an immunologically privileged site and providing cell stimulatory factors in a mammal for transplants is also carried out. A method of co-localizing islet cells with Sertoli cells and the use of the co-localized product for treating diabetes mellitus is further provided. Further described is a method of creating systemic tolerance to foreign antigens. A method of enhancing the viability, maturation, proliferation of functional capacity of cells in tissue culture is also provided. In addition, pharmaceutical compositions comprising Sertoli cells and cells that produce a biological factor, and/or a pharmaceutically acceptable carrier are further provided.

37 Claims, 12 Drawing Sheets

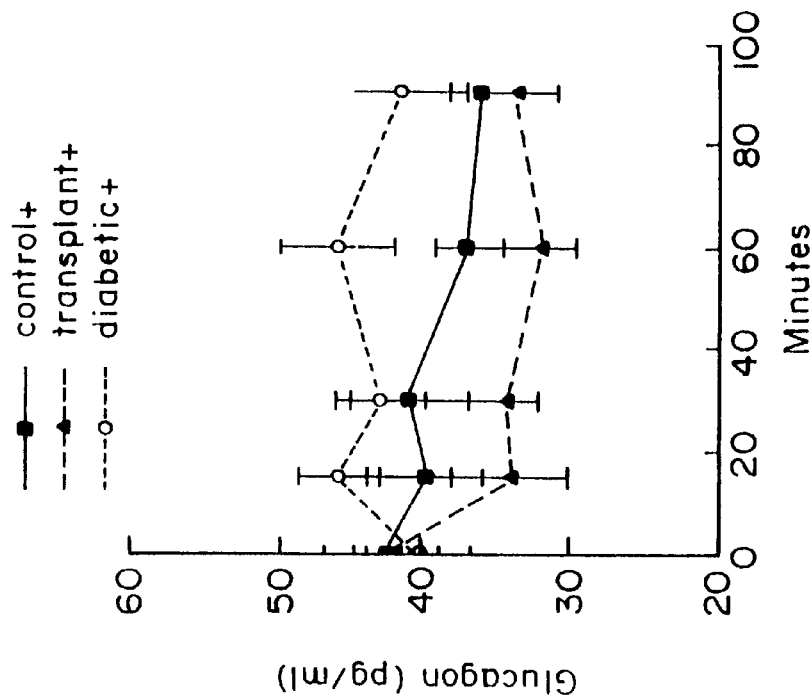
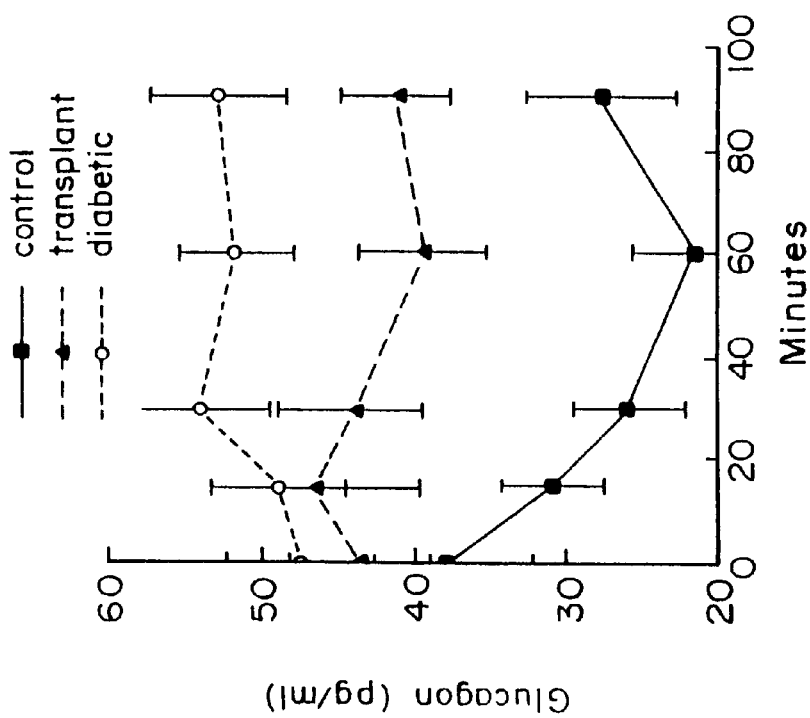

TREATMENTS USING SERTOLI CELLS

CROSS-REFERENCE OF RELATED APPLICATIONS

The present application is a divisional of application Ser. No. 08/660,258 filed Jun. 7, 1996, now U.S. Pat. No. 5,958,404, which is a continuation-in-part of application Ser. No. 08/485,340 filed Jun. 7, 1995, now U.S. Pat. No. 5,849,285, which is a continuation-in-part of application Ser. No. 08/421,641 filed Apr. 13, 1995, now U.S. Pat. No. 5,725,854, which is a continuation-in-part of application Ser. No. 08/211,695 filed on Apr. 13, 1994, now abandoned.

This invention was made with United States government support under grant DK42421 awarded by the National Institutes of Health. The United States Government may have certain rights in the invention.

FIELD OF THE INVENTION

Transplants of healthy organs or cells into a patient suffering from a disease are often rejected by the body due to an immune response initiated in response to the foreign tissue or cells. The present invention provides a method of cellular transplantation in which an immunologically privileged site is created and cell stimulatory factors are produced, thus alleviating the rejection associated with conventional transplantation therapy. Specifically, the present invention describes a method of treating a disease that results from a deficiency of a biological factor which comprises administering to a mammal Sertoli cells and cells that produce the biological factor. In particular, the present invention describes a method of treating diabetes mellitus by transplanting pancreatic islet of Langerhans cells in conjunction with Sertoli cells to create an immunologically privileged site and to provide pancreatic islet cell stimulatory factors. A method of creating an immunologically privileged site and providing cell stimulatory factors in a mammal for transplants is further described by the present invention. A method of creating systemic tolerance to transplants is further provided by the present invention. The present invention further describes a method of enhancing the maturation, proliferation and functional capacity of cells in tissue culture by co-culturing these cells with Sertoli cells. A method of enhancing the recovery rate and viability of frozen cells, and in particular factor producing cells, in tissue culture by co-culturing these cells with Sertoli cells is also described herein. Another aspect of the present invention is directed to a method of co-localizing Sertoli cells with cells that produce a biological factor for treating diseases caused by a deficiency thereof, e.g., encapsulating islet cells which produce insulin with Sertoli cells. The use of the co-localized, e.g., encapsulated Sertoli cells and islet cells for treating diabetes mellitus is further described by the present invention. A pharmaceutical composition comprising Sertoli cells and cells that produce a biological factor is also provided.

BACKGROUND OF THE INVENTION

Certain chronic diseases destroy the functional cells in affected organs. Mammals with such diseases are often unable to produce proteins or hormones necessary to maintain homeostasis and usually require numerous exogenous substances to survive. Transplanting healthy organs or cells into a mammal suffering from such a disease may be necessary to save the mammal's life. This type of therapy is generally regarded as a last alternative to curing an otherwise fatal condition. Such transplants, however, are often rejected by the body due to an immune response initiated in response to the foreign tissue or cells. Presently, the only recourse to combat this immune response is to administer chronic nonspecific immunosuppression agents. Unfortunately, this only trades the complications of one chronic disease with other complications caused by the immunosuppression agent.

One disease which scientists have attempted to treat with organ and/or cellular transplants but have had very limited success is diabetes mellitus. Diabetes mellitus is a prevalent degenerative disease in mammals. It is characterized by a relative or complete lack of insulin secretion by the beta cells within the islets of Langerhans of the pancreas or by defective insulin receptors.

This insulin deficiency prevents normal regulation of blood glucose levels and often leads to hyperglycemia and ketoacidosis. When administered to a mammal, insulin promotes glucose utilization, protein synthesis, formation and storage of neutral lipids and the growth of certain cell types.

In the United States alone there are approximately 13 million diabetics. Of these, 2.6 million are insulin dependent diabetics. *Drug & Market Dev.*, 4:210 (1994). Health care analysts estimate that diabetes costs $92 billion a year resulting from medical costs and lost productivity.

The various forms of diabetes have been organized into a series of categories developed by the National Diabetes Data Group of the National Institutes of Health. Type I diabetes in this classification scheme includes patients dependent upon insulin to prevent ketosis. This group of diabetics was previously called juvenile-onset diabetes, brittle diabetes or ketosis-prone diabetes. Type I diabetes is caused by an autoimmune reaction that causes complete destruction of beta cells.

Type II diabetes is classified as adult-onset diabetics. The diabetic patient may or may not be insulin dependent. Type II diabetes can be caused by a number of factors. For most mammals with Type II diabetes, the beta islet cells are defective in the secretion of insulin.

There are many therapies currently used to treat diabetes, however, each has its limitations. The major problem confronting most patients with diabetes mellitus is that currently available therapies fail to prevent the complications of the disease process. The most common method of treating Type I diabetes in mammals is providing an endogenous source of insulin such as porcine, bovine or human insulin. Insulin injection therapy prevents severe hyperglycemia and ketoacidosis, but does not completely normalize blood glucose levels. This treatment further fails to prevent the complications of the disease process, including premature vascular deterioration. Premature vascular deterioration is the leading cause of morbidity among diabetic patients. Furthermore, complications resulting from long-term diabetes include renal failure, retinal deterioration, angina pectoris, arteriosclerosis, myocardial infarction and peripheral neuropathy.

A second method of treating diabetes is by transplanting the pancreas in conjunction with the administration of chronic nonspecific immunosuppression agents. This treatment is usually given to an individual who has advanced diabetes, such as an individual with kidney failure. Whole pancreas transplantation can be successfully done with a 75% one year survival rate, but surgical transplantation of the pancreas is very difficult. Furthermore, since the entire organ must be donated, the only practicable source is a deceased donor. In addition, when cyclosporine, the most common immunosuppressive drug used for organ transplants, is administered in a dosage necessary to suppress the immune response, the drug inhibits pancreatic cell function. Furthermore, the steroids that are often administered with an organ transplant often cause the patient to become diabetic.

A third treatment involves transplanting islet of Langerhans cells into the diabetic patient. However, islet transplantation has been generally unsuccessful due to the aggressive immune rejection of islet grafts. (Gray, 1991, *Immunology Letters* 29:153; Jung et al., 1990, *Seminars in Surgical Oncology* 6:122). In particular, successful transplantation of isolated pancreatic islet cells has been very difficult to achieve due to the chronic administration of immunosuppressive drugs required to prevent organ rejection of the cells following transplantation. These dosages of immunosuppressive drugs can cause increased susceptibility to infection, hypertension, renal failure and tumor growth. Furthermore, unlike most organ transplants, islet cells must grow their own blood supply following implantation in the host in order for the cells to survive. Conventional transplantation techniques do not provide the necessary factors to stimulate the production of new blood vessels.

Thus, to successfully transplant cells in a mammal, it is necessary that the cellular transplants are not rejected by the recipient and have the capacity to grow upon transplantation. As a commercial reality, it is further necessary that a sufficient quantity of cells are available for transplantation. Traditionally, the number of cellular transplants have been limited by the inability to adequately collect and store a sufficient number of cells for transplantation. Conventional storage techniques, such as cryopreservation, often damage a large quantity of the stored cells. Porcine islet cells, for example, are extremely fragile and easily dissociate into fragments or single cells upon thawing.

The present invention alleviates many of the problems associated with the current therapies for chronic diseases that destroy the functional cells of vital organs. Specifically, the present invention provides a method of creating systemic tolerance to subsequent transplants in the mammal. Furthermore, the present invention solves the problems associated with the conventional therapies for diabetes mellitus, by providing a method of transplanting pancreatic islets cells into a diabetic mammal, whereby the cellular transplants produce insulin in the diabetic mammal. The present inventor has previously demonstrated extended functional survival of islet cells allografts and xenografts in the testis. (Selawry et al., 1989, *Diabetes* 38:220.) It has been surprisingly discovered in accordance with the present invention that an immunologically privileged site can be created in a mammal by transplanting Sertoli cells to a nontesticular site in a mammal. The newly created immunologically privileged site allows the transplantation and survival of cells that produce biological factors useful in the treatment of diseases, especially diabetes. In addition to creating an immunologically privileged site, the Sertoli cells produce cell stimulatory factors which enhance the maturation, proliferation and functional capacity of cells. Sertoli cells have further been found to enhance the recovery rate and viability of mammalian cells stored by techniques such as cryopreservation.

SUMMARY OF THE INVENTION

The present invention relates to a method of treating a disease that results from a deficiency of a biological factor in a mammal which comprises administering Sertoli cells and cells that produce the biological factor. In a preferred embodiment, the biological factor is a hormone.

In a more preferred embodiment, the disease is diabetes mellitus, the factor producing cells are pancreatic islet cells and the factor is insulin.

In yet another embodiment the cells that produce the biological factors are cells that have been genetically engineered, for example by transformation with a nucleic acid that expresses the biological factor.

The present invention further relates to a method of treating diabetes mellitus in a mammal comprising administering pancreatic islet cells and Sertoli cells. In a preferred embodiment the Sertoli cells and islet cells are administered by transplantation. The Sertoli cells may be isolated from a mammal or they may be derived from a Sertoli cell line, in accordance with the present invention.

Another aspect of this invention is directed to a method of creating an immunologically privileged site and producing cell stimulatory factors in a mammal.

A further aspect of the present invention is directed to a method of creating systemic tolerance to a subsequent transplant in a mammal by transplanting Sertoli cells prior to said subsequent transplant.

Still a further aspect of the present invention provides a method of enhancing the maturation, proliferation and functional capacity of cells in tissue culture by co-culturing these cells with Sertoli cells.

A method of enhancing the recovery rate and viability of frozen mammalian cells and in particular factor producing cells, in tissue culture by co-culturing these cells with Sertoli cells is further provided by the invention described herein.

Another aspect of the present invention is directed to a method of co-localizing, e.g., encapsulating the biological factor producing cells, e.g., islet cells, with Sertoli cells and to the use of the co-localized product for enhancing long-term immunoprotection and nutritional survival of islets and for the treatment of diabetes.

Yet another embodiment of the present invention provides a pharmaceutical composition comprising Sertoli cells and cells that produce a biological factor. In a preferred embodiment the pharmaceutical composition comprises Sertoli cells and pancreatic islet-cells and a pharmaceutically acceptable carrier.

The present invention further provides a compartmentalized kit containing Sertoli cells and cells that produce a biological factor. An article of manufacture comprising a packaging material and Sertoli cells contained within the packaging is also provided.

BRIEF DESCRIPTION OF THE DRAWINGS

FIG. 5a shows the plasma glucose (mg/dl) concentrations in response to the oral glucose administration of 2 g/kg of a 50% glucose solution in three groups of rats: untreated control Sprague Dawley, transplanted diabetic BB/Wor dp, and insulin treated diabetic BB/Wor dp rats. FIG. 5b shows the serum insulin levels in response to the same dose of oral glucose in untreated control Sprague Dawley, and in transplanted BB/Wor dp rats.

FIGS. 6a and 6b show the effect of intratesticular islet allografts on plasma glucagon secretory responses to oral glucose and a combination of glucose plus glipizide in spontaneously diabetic BB/Wor dp rats. FIG. 6a shows the plasma glucagon responses to the oral administration of 2 g/kg of a 50% glucose solution in three groups of rats: untreated control Sprague Dawley, transplanted diabetic BB/Wor dp, and insulin treated diabetic BB/Wor dp rats. FIG. 6b shows the plasma glucagon responses to the oral administration of 7 mg/kg of glipizide and 2 g/kg of a 50% glucose solution, administered 30 minutes later, in three groups of rats: untreated control Sprague Dawley, transplanted diabetic BB/Wor dp, and insulin treated diabetic BB/Wor dp rats. Data points are mean ±SE of eight animals in each group.

DETAILED DESCRIPTION OF THE INVENTION

Figure 1:
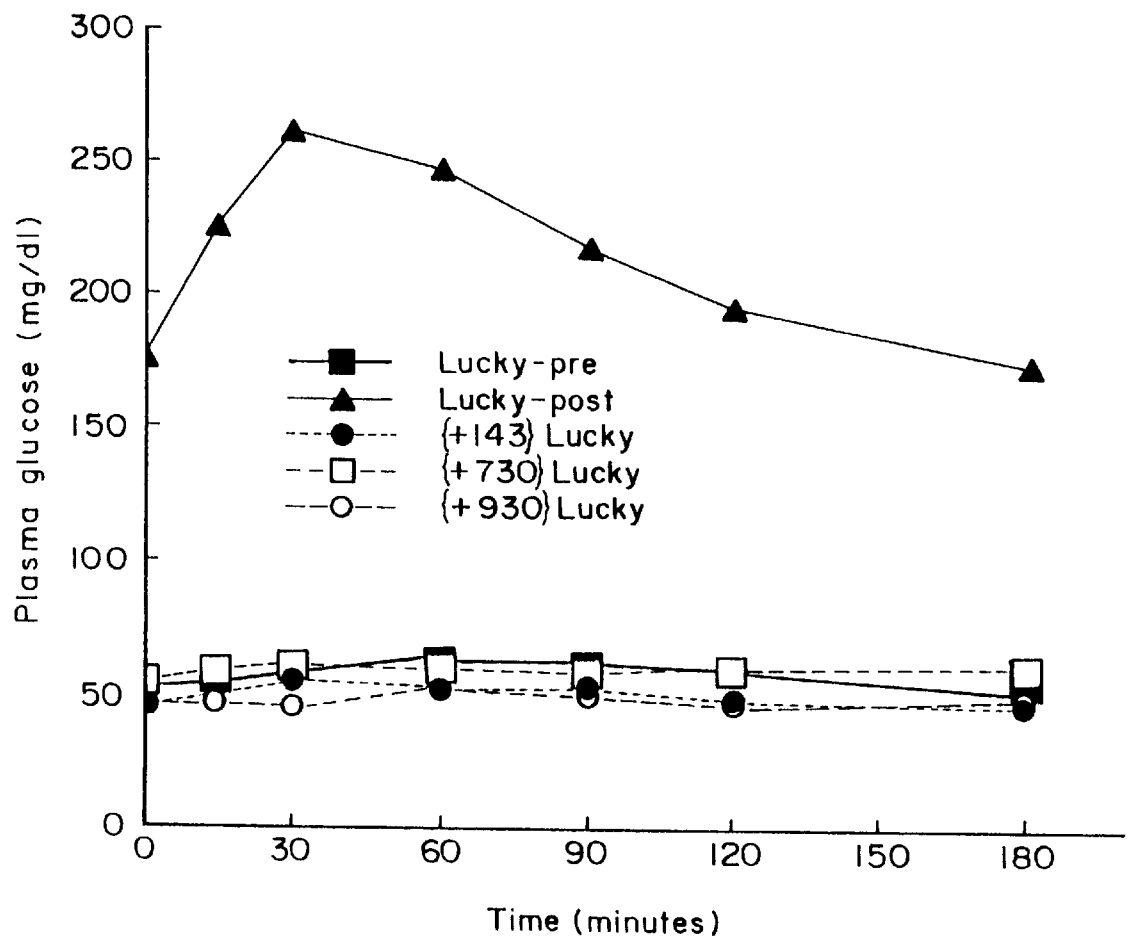
FIG. 1 shows the glucose responses to oral sustacal tolerance tests done on the monkey "Lucky" at intervals before pancreatectomy (Lucky-pre); after pancreatectomy but prior to transplantations (Lucky-post); and at intervals following transplantation (143 days, 730 days and 930 days, respectively).

The present invention is directed to a method of treating a disease that results from a deficiency of a biological factor in mammals which comprises administering to a mammal Sertoli cells and a therapeutically effective amount of cells that produce the biological factor. As defined by the present invention, a biological factor is a protein or nonprotein compound that is necessary for cellular metabolism and homeostasis. In a preferred embodiment, the biological factor is a hormone. Hormone producing cells which can be administered using the method described in the present invention include, for example, pancreatic islet of Langerhans, pituitary, liver, parathyroid, thyroid and ovarian cells.

In accordance with the present invention, the Sertoli cells and the cells that produce the biological factor can be from the same species as the mammal to be treated or from a different species. Further, the Sertoli cells and the cells that produce the biological factor need not be derived from the same species. It has been demonstrated in accordance with the present invention that Sertoli cells from pigs in conjunction with islet of Langerhans from pigs can be used in the treatment of diabetes mellitus in rats. In a preferred embodiment the Sertoli cells are bovine, porcine or human.

Sertoli cells, which are the predominant cells of male testes, used in the method described by the present invention can be separated from other testicular cells such as Leydig cells, peritubular cells and germ cells, using conventional techniques. For example, the testes of a male mammal, such as a boar or ram, are first collected by castration. The testes are then chopped into several pieces and subsequently washed by centrifugation.

Testicular Leydig cells can be removed from the tissue suspension using digestion agents such as trypsin and DNase. The remaining cell suspension is then washed by centrifugation several times. The pellet is resuspended in collagenase, incubated and washed by centrifugation to eliminate peritubular cells within the testes. Testicular germ cells can be removed by incubating the pellet with hyaluronidase and DNase. After several washings by centrifugation, the Sertoli cells are collected to transplant using the method of the present invention.

In accordance with the present invention, the Sertoli cells may be obtained by various methodologies which establish a line of cells derived from primary cultures of mammalian Sertoli cells. In one embodiment the Sertoli cells are immortalized with a chemical or viral transformant, e.g., a temperature-sensitive mutant of the SV40 virus that allows propagation and promotes differentiation of the cells. In another embodiment Sertoli cells are isolated from mammalian tissue by conventional means using various hydrolytic enzymes such as collagenase, hyaluronidase, and the like. The cells are further isolated from the tissue by such conventional methods as filtering and centrifugation to obtain a purified Sertoli cell population. The isolated and purified Sertoli cells are next incubated and conventionally immortalized under conditions known in the art such as treating said cells with a chemical, that transforms the DNA thereof, e.g. a mutagen. Examples include N-nitrosylmethylureas, nitrous acid, hypoxanthine, nitrosamines (see, Freshney, I. R. in *Culture of Animal Cells, A Manual of Basic Technique*, 3 ed., Chapter 15, Wiley-Liss, New York). Alternately, the isolated purified sertoli cells are incubated in a virus-containing medium consisting of, e.g., SV40 virus or polyoma virus and a conventional growth medium such as F12/DMEM, for sufficient time to propagate the Sertoli cells, which are then isolated from the virus. If an infectious virus cell is being utilized, then it is preferred that the virus be attenuated by techniques known in the art. The Sertoli cells may be isolated from the virus or chemical by conventional techniques employing hydrolytic enzymes. To verify that the Sertoli cells are produced by this methodology, the isolated Sertoli cells are optionally screened for the expression of an appropriate isolate for cloning, e.g., on the basis of expression of mRNAs encoding Sertoli cell-secreted proteins.

In accordance with the present invention, a biological factor is a protein or nonprotein compound that is absent, deficient or altered in a disease state. Cells that produce a biological factor can be isolated, for example, by first surgically removing the tissue that produces the factor from a mammal. This tissue is subsequently chopped and digested using conventional techniques. For example, the tissue can be digested using a collagenase digestion. The particular factor producing cells can subsequently be collected from the digestion mixture using a separation gradient such as a Ficoll gradient. The factor producing cells are then grown in tissue culture in serum using conventional techniques.

In accordance with the present invention, the factor producing cells may be co-cultured with Sertoli cells in tissue culture. Furthermore, factor-producing mammalian cells may be co-cultured, co-localized or co-transplanted with Sertoli cells to enhance the maturation, proliferation and functional capacity of the mammalian cells. It has been demonstrated in accordance with the present invention that the maturation of porcine islet cells was enhanced when these cells were co-cultured with Sertoli cells as evidenced by both the structural integrity and functionality of the porcine islet cells compared to the islet cells cultured without Sertoli cells. Thus, maturation is defined by the present invention as the process by which a cell develops and becomes functional. The enhanced proliferation of porcine islet cells co-cultured with Sertoli cells is evidenced by the larger number of viable, insulin producing cells compared to porcine islet cells cultured without Sertoli cells. Proliferation as used herein, is defined as a process in which cells multiply. The enhanced functional capacity of porcine islet cells cultured with Sertoli cells is evidenced by the greater capacity of the co-cultured islet cells to respond to glucose and glucose plus Forskolin as insulin secretagogues. Functional capacity is defined as the ability of a cell to respond the biological environment and to generate various chemical and biological substances in response to the various substances present in the biological environment (e.g. when islet cells produce insulin in the presence of glucose).

Mammalian cells which can be co-cultured, co-localized or co-transplanted with Sertoli cells as described by the present invention include, for example, germ cells, such as sperm cells, oocytes, ovarian cells and zygotes; endocrine cells, such as pancreatic islet cells, chromaffin, thyroid cells, hepatocytes, parathyroid cells, Leydig cells, follicular cells; hybridoma cells; recombinantly transformed cells; epithelial cells; nerve cells and epidermal cells. In a preferred embodiment, the mammalian cell is a germ cell or endocrine cell. Cells grown in tissue culture can be transplanted into a mammal in conjunction with the Sertoli cells using the methods of the present invention. In accordance with the present invention, factor producing cells may be stored using a variety of conventional techniques, such as cryopreserving the cells prior to growth in tissue culture for subsequent transplantation. It has been observed in accordance with the present invention, that Sertoli cells co-cultured, co-localized or co-transplanted with mammalian cells, and in particular factor producing cells such as islet cells, enhance the recovery rate and viability of the mammalian cells in tissue culture and in particular, enhance the recovery rate and viability of cells that have been previously stored using techniques such as cryopreservation. Moreover, when co-localized with factor producing cells, such as islet cells, Sertoli cells provide immunoprotection and nutritional support when the two cell types are proximally located. Sertoli cells protect the factor producing cells, such as islets, from, inter alia, macrophages, proteins, lymphokines (e.g., IL-1) and toxic factors released by activated lymphocytes. Sertoli cells provide nutritional support for islets through Sertoli secreted growth factors, e.g., IGF (insulin-like growth factor), EGF (epidermal growth factor) and transferrin, thereby permitting the factor-producing cells to survive longer than when the Sertoli cells are not present.

In a preferred embodiment the factor is a hormone, and the hormone producing cells are isolated from a tissue source as described above. For example, insulin-producing cells are isolated from the pancreas. In another preferred embodiment, the factor producing cells are provided by transforming suitable host cells with a nucleic acid capable of expressing the factor of interest. Transformed cells are provided by methods known to one of ordinary skill in the art, and can be found in a myriad of textbooks and laboratory mammals, including Sambrook et al. (1989) Molecular Cloning: A Laboratory Mammal, Cold Spring Harbor Laboratories, Cold Spring, New York. If necessary, the nucleic acid encoding the factor of interest can be adapted by methods known to one of ordinary skill in the art to effect secretion of the factor from the transformed cell. The utilization of Sertoli cells in conjunction with the factor producing cells in accordance with the method of the present invention allows the production of an immunologically privileged site and production of cell stimulatory factors in the treated mammal.

The administration of factor producing cells and Sertoli cells into a mammal is accomplished by conventional techniques. In a preferred embodiment, administration is by transplantation and the factor producing cells are injected into the mammal concurrently with or immediately after the injection of the Sertoli cells into the same site. In another embodiment, Sertoli cells and cells producing the biological factor are co-localized and administered to a mammal. As an example, islets and Sertoli cells are co-encapsulated and injected into the mammal intraperitoneally. In another embodiment, co-localized islets and Sertoli cells are transplanted, injected or provided into a biological or non-biological biocompatible material (biomaterial). Examples of a biological biocompatible material include an isolated segment of small intestine with intact circulation, a pouch (e.g. an omental pouch or a gastric pouch etc.), a biocompatible polymeric scaffold, a polymeric sponge or matrix, and the like, prepared pursuant to conventional techniques. On the other hand, a non-biological, biocompatible material includes reticulated thermoplastics such as acylnitrile vinyl chloride copolymer (PAN-PVC), and the like. The biomaterial may be conventionally implanted in a mammal. In accordance with the present invention, an exogenous biological factor may be administered following the transplantation of factor producing cells and Sertoli cells until the transplanted cells produce a therapeutically effective amount of the biological factor. For the treatment of diabetes, for example, insulin may be administered following the transplantation of pancreatic islet cells and Sertoli cells until the transplanted islet cells produce a therapeutically effective amount of insulin.

The Sertoli cells and factor producing cells of the present invention can be transplanted or co-localized using any technique capable of introducing the cells into the mammal such as parenteral administration, subcutaneous administration following surgical exposure to a desired site, biocompatible scaffold, sponge or matrix delivery or intraperitoneal administration. Prior to transplantation, the recipient mammal is anesthetized using local or general anesthesia according to conventional technique. In a preferred embodiment the mammal to be treated is human. In another embodiment the present method of treating disease further comprises administering an immunosuppressive agent such as, for example, cyclosporine, tacrolimus, despergualin and monoclonal antibodies to, e.g., T cells. In a preferred embodiment the immunosuppressive agent is cyclosporine. In another preferred embodiment cyclosporine is administered at a dosage of from 0.5 mg to 200 mg/kg body weight. In a most preferred embodiment cyclosporine is administered at a dosage of from 5 mg to 40 mg/kg body weight.

It has been discovered in accordance with the present invention that administration of Sertoli cells results in the creation of an immunologically privileged site in the treated mammal and in the production of cell stimulatory factors. An immunologically privileged site as defined by the present invention is a site in the mammal where the immune response produced in response to the transplanted cells is suppressed due to immuno-suppressive agents produced by Sertoli cells. Immunologically privileged sites are characterized by an available blood supply to provide nourishment for the transplanted cells and a dense tissue to keep the transplanted cells within close proximity of each other. Examples of immunologically privileged sites as defined by the present invention include the renal subcapsular space, subcutaneous facie, the brain and the hepatic portal vein. Cell stimulatory factors are defined by the present invention as factors that enhance the viability of mammalian cells. For example, it has been shown in accordance with the present invention that Sertoli cells increase the rate at which the transplanted factor producing cells vascularize in the transplanted site (i.e. promote angiogenesis). Further, it has been shown by the present invention that these cell stimulatory factors enhance the maturation, proliferation and functional capacity of cells transplanted with Sertoli cells. It is therefore indicated that the Sertoli cells produce cell stimulatory factors which enhance of viability of mammalian cells as evidence, for example, by the increased vascularization rate of the transplanted islet cells. As used herein, viability denotes the number of living cells in a preparation.

In a preferred embodiment, the present invention describes a method of treating diabetes mellitus by transplanting islet of Langerhans in conjunction with Sertoli cells to create an immunologically privileged site. Allografts as used in the present invention describes the transfer of tissues or cells between two genetically dissimilar mammals of the same species. The term xenografts in the present invention describes the transfer of tissues or cells between two mammals of different species.

The transplanted islet of Langerhans cells and Sertoli cells used in the method described by the present invention can be prepared using any number of conventional techniques. For example, islet of Langerhans cells can be prepared from the pancreas of several mammals of the same species. The pancreases are pooled together, chopped up and digested using collagenase. The islet of Langerhans cells can be further isolated using conventional gradients. Once isolated, the islet cells can be grown in culture and then transplanted in conjunction with Sertoli cells to create an immunoprivileged site.

Sertoli cells used in the method described by the present invention can be derived from primary cultures of mammalian Sertoli cells according to the methods known to one skilled in the art including the method of e.g. Roberts et al. (1995) Biology of Reprod. 53:1446–1453, the contents of which is incorporated herein by reference, or the Sertoli cells can be isolated from mammalian male testes. To collect the islet cells, the testes are first chopped into several pieces and then washed by centrifugation. Leydig cells, present in the crude mixture, can be removed from the tissue suspension using digestion agents such as trypsin and DNase. The remaining cell suspension is then washed by centrifugation several times. Following, the pellet may be resuspended in collagenase, incubated and washed by centrifugation to eliminate peritubular cells within the testes. Testicular germ cells can be removed by incubating the pellet with hyaluronidase and DNase. After several washings by centrifugation, the Sertoli cells for transplantation can be collected.

The Sertoli cells can be transplanted to create an immunoprivileged site within a mammal using a variety of techniques. For example, after the mammal is anesthetized, the Sertoli cells can be injected into a tissue mass, thereby creating an immunoprivileged site. The Sertoli cells and factor producing cells of the present invention can be combined using the techniques capable of co-localizing the cells such as microencapsulation inside biocompatible membranes, hydrogels, or reticulated thermoplastics, for example. The co-localized cells can subsequently be injected, transplanted or provided into a tissue mass subcutaneously or into a pouch, e.g. an intestinal pouch, an omental pouch, a gastric pouch, or a biocompatible polymeric scaffold, sponge or matrix consisting of, e.g., polylacetic acid. Once injected, transplanted, or provided, the co-localized product is used to treat diseases caused by a deficiency of the biological factor. For example, the Sertoli cells and islet cells in combination are useful in treating diabetes mellitus.

Sertoli cells are administered in an amount effective to provide an immunologically privileged site. Such an effective amount is defined as that which prevents immune rejection of the subsequently or co-administered cells that produce the biological factor. Immune rejection can be determined for example histologically, or by functional assessment of the factor produced by the cells.

The present invention further provides a method of creating systemic tolerance to a subsequent transplant in a mammal by transplanting Sertoli cells prior to said subsequent transplant as described herein. A transplant as used herein is a mammalian cell, tissue, organelle or organ that is removed from one mammal and placed in the same or different mammal. The subsequent transplant may be made in the same site or a secondary site. A secondary site as used herein, is a transplantation site in the mammal different from the initial transplantation site. Systemic tolerance is demonstrated by various biological phenomena. For example, systemic tolerance results in a diminished destructive immune response to a subsequent allograft or xenograft in a mammal without the administration of prolonged immunosuppressive agents or the co-transplantation of Sertoli cells. In accordance with the present invention, the allograft or xenograft may be any type of transplant, including cells, tissues, organelles or an organ. The types of cells which may be transplanted in accordance with the methods described by the present invention include, for example, endocrine cells, bone marrow cells, hepatocytes or liver cells, nerve cells or brain cells, and islet cells (fetal, neonatal or adult). The types of tissues, organelles or organs which may be transplanted in accordance with the methods described by the present invention include, for example, heart, kidney, pancreas, liver, skin, ligaments, tendons and cartilage.

As demonstrated by the present invention, a mammal may be tolerized (i.e. systemic tolerance may be achieved) by a variety of procedures. For example, systemic tolerance may be achieved by transplanting an allograft or xenograft with Sertoli cells and subsequently transplanting the same type of allograft or xenograft without Sertoli cells or a prolonged administration of immunosuppressive agents. Systemic tolerance may also be achieved by transplanting an allograft of any cell, tissue, organelle or organ without Sertoli cells or prolonged immunosuppressive agents following an initial transplantation of an allograft with Sertoli cells. In a preferred embodiment Sertoli cells are administered in amounts ranging from $10^1$ to $10^{10}$ cells. In a more preferred embodiment, $10^5$ to $10^{10}$ cells are administered.

The cells producing the biological factor are administered in a therapeutically effective amount. The ordinary skilled artisan can determine the appropriate amount of cells producing the biological factor by methods known in the art. The amount of cells is dependent upon the amount of factor being produced by the cells and the known therapeutically effective amount of the factor necessary to treat the disease. For example, 1 to 1000 islet cells per gram body weight can be administered to treat diabetes using allografts, 20 to 1000 islets per gram body weight are administered using xenografts. In another preferred embodiment, 5 to 100 islet cells per gram body weight are administered to treat diabetes. In a most preferred embodiment, 5 to 20 islet cells per gram body weight are administered, using allografts and 100–1000 islet cells per gram body weight are administered for xenografts.

In another embodiment the present method of treating diabetes further comprises administering an immunosuppressive agent such as, for example, cyclosporine, tacrolimus, despergualin and monoclonal antibodies to, e.g., T cells. In a preferred embodiment the immunosuppressive agent is cyclosporine. In another preferred embodiment cyclosporine is administered at a dosage of from 0.5 mg to 200 mg/kg body weight. In a most preferred embodiment cyclosporine is administered at a dosage of from 5 mg to 40 mg/kg body weight.

More generally, the immunosuppressive agent can be administered for a time sufficient to permit the transplanted islets to be functional. This period extends from the point prior to or immediately following the transplantation of the islets to the point at which the cells are capable of producing therapeutically effective amounts of insulin. In a preferred embodiment, the sufficient period of time to administer an immunosuppressive agent is about 40 to about 100 days following transplantation of the islets. In a more preferred embodiment, the sufficient period of time is about 50–60 days.

A preferred embodiment of this invention is directed to a method of treating Type I and Type II diabetes mellitus by transplanting islet of Langerhans in conjunction with Sertoli cells into the renal subcapsular space.

Unlike the therapies for diabetes described in the prior art, the method of treating diabetes described by the present invention prevents the complications of the disease process and does not result in the adverse side effects associated with conventional diabetes therapy. Furthermore, the method of transplanting islet cells described by the present invention provides the necessary factors for angiogenesis, growth enhancing and increased functional capacity of the islet transplants.

A method of creating an immunologically privileged site in a mammal is further described by the present invention. An immunologically privileged site is created by transplanting isolated Sertoli cells into a mammal in an amount effective to create an immunologically privileged site. In a preferred embodiment, $10^1$ to $10^{10}$ cells are administered. In a more preferred embodiment, $10^5$ to $10^{10}$ cells are administered. In a preferred embodiment the Sertoli cells are transplanted into the renal subcapsular space or subcutaneous facie by injection. In a preferred embodiment the mammal is a human and the Sertoli cells are human or porcine.

A further aspect of the present invention is directed to a method of enhancing the recovery rate and viability of frozen mammalian cells in tissue culture comprising co-culturing the frozen mammalian cell with Sertoli cells. As shown in accordance with the present invention, Sertoli cells produce cell stimulatory factors which enhance the recovery rate and viability of mammalian cells previously frozen. Mammalian cells may be frozen using a widely conventional techniques, including, for example, cryopreservation.

Further contemplated in accordance with the present invention is a method of enhancing the recovery and proliferation of ex vivo cells comprising co-culturing said cells with Sertoli cells for a time and under conditions sufficient to achieve said enhanced recovery and proliferation.

Another aspect of the present invention provides a pharmaceutical composition comprising Sertoli cells and cells producing a biological factor and a pharmaceutically acceptable carrier. In a preferred embodiment the composition comprises Sertoli cells and islet of Langerhans cells and a pharmaceutically acceptable carrier. A further preferred embodiment of the present invention comprises using porcine, bovine or human Sertoli cells and porcine, bovine or human islet of Langerhans cells. As used herein, a pharmaceutically acceptable carrier includes any and all biological and non-biological biocompatible membrane materials. A pharmaceutically acceptable carrier also includes any conventional solvents, dispersion media, coatings, antibacterial and antifungal agents, isotonic agents and the like. The use of such media and agents is well-known in the art.

The present invention further contemplates a pharmaceutical composition comprising Sertoli cells and a pharmaceutically acceptable carrier. This pharmaceutical composition, upon administration to a mammal, can be used to treat a variety of diseases, such as for example, autoimmune diseases. Accordingly, the present invention is further directed to treating an autoimmune disease in a mammal comprising administering a therapeutically effective amount of Sertoli cells to the mammal.

The present invention is further directed to a method of enhancing the recovery and proliferation of ex vivo cells comprising culturing said cells with a culture media from a tissue culture containing Sertoli cells for a time and under conditions sufficient to achieve said enhanced recovery and proliferation. As contemplated by the present invention, Sertoli cells are cultured using a conventional tissue culture media as described herein for a time and under conditions sufficient for the Sertoli cells to produce, for example, cell stimulatory factors. The Sertoli cells are then removed from the culture media and the culture media is used in subsequent tissue cultures, for example, as a culture media for sperm cells previously stored by cryopreservation.

Another aspect of the present invention is directed to methods of co-localizing biological factor producing cells, e.g., islets of Langerhans, with Sertoli cells to enhance long-term immunoprotection and nutritional survival of transplanted factor producing cells, e.g., islets. The methods of co-localization include co-localization in an intestinal segment, pouch, e.g. an omental pouch, a gastric pouch or biocompatible polymeric scaffold, sponge or matrix, for example. The method of co-localization in an intestinal segment comprises:

(a) isolating a segment of mammalian small intestine with intact mucosa and intact circulation;

(b) removing the mucosal layer of the small intestine and closing the ends of the isolated segment;

(c) implanting biological factor producing cells and Sertoli cells into the isolated segment; and (d) fixing the isolated segment to the small intestine.

Methods of co-localizing biological factor producing cells, e.g., islets with Sertoli cells in pouches, such as omental or gastric pouches are also contemplated by the present invention as described by Amiri, et al. (1990) Arch. Surg. 125:1472–1474 and Bayat, et al. (1995) Surg. Res. Commun. 17:87–91, both of which are incorporated herein by reference. Procedures for co-localizing islets and Sertoli cells in biologically compatible pouches are general and conventionally employed on a case-by-case basis by the skilled artisan in accordance with the present invention.

Procedures for co-localizing islets and Sertoli cells in polymeric scaffolds are readily appreciated by the skilled artisan. It is preferred that the polymeric templates used in accordance with the present invention are biodegradable and comprise a polyvinyl alcohol, e.g., poly-L-lactic acid. Polyvinyl alcohol based templates provide sufficient porosity to permit rapid tissue ingrowth and prevascularization before cell transplantation. In essence, the polymeric template employed in connection with the present invention acts as a matrix or sponge permitting the ingrowth of blood vessels and tissue which facilitates the co-localization of, e.g., islets and Sertoli cells by providing ready access to a nutrient-rich blood supply.

It is preferred that the Sertoli cells are provided in an amount ranging from about $10^1$ to about $10^{10}$ cells. In a more preferred embodiment, Sertoli cells are provided in an amount ranging from about $10^4$ to about $10^{10}$ cells. In yet another preferred embodiment, the factor producing cells are pancreatic islets. The islets are provided in a preferred amount of about 5 to about 200 cells per gram of body weight, and in a more preferred amount of about 5 to about 100 cells per gram of body weight.

A further aspect of the present invention is directed to a method of encapsulating biological factor producing cells, e.g., islets, with Sertoli cells to enhance long-term immunoprotection and nutritional survival of transplanted islets. The method of encapsulation comprises:

(a) suspending a pharmaceutically effective amount of biological factor producing cells, e.g., islets, and Sertoli cells in combination with a gelling effective amount of a first water soluble gelling agent in an aqueous medium which is physiologically compatible with the cells and extruding the islet/Sertoli cell/gelling agent mixture to form a droplet containing the islets and Sertoli cells;

(b) subjecting the product of step (a) to an effective amount of network forming cations to form discrete capsules of sufficient size to encapsulate the islets and Sertoli cells together;

(c) forming a semipermeable membrane around the capsules to obtain a single-walled bead encapsulating the cells; and (d) contacting the single-walled bead with a gelling effective amount of a second gelling agent so as to form a second semi-permeable membrane encapsulating the product of step (c).

The gelling agent may be any water-soluble material which can be gelled to form a bead. A preferred gelling agent is a water soluble, natural or synthetic polysaccharide gum such as an alkali metal alginate. A preferred gum is sodium alginate. Other gums which may be used include guar gum, gum arabic, carrageenan, pectin, tragacanth gum, xanthan gum or their acidic fractions.

In a preferred embodiment, the Sertoli cells and factor producing cells are encapsulated within an alginate polylysine-alginate semi-permeable hydrogel. It is preferred that the Sertoli cells are derived from bovine, porcine, and human sources and are produced by a cell line in accordance with the present invention. It is preferred that the Sertoli cells are provided in an amount of from $10^1$ to $10^{10}$ cells. In a more preferred embodiment, Sertoli cells are provided in an amount of from about $10^4$ to $10^{10}$ cells. In yet another preferred embodiment the factor producing cells are pancreatic islets. The islets are provided in a preferred amount of about 5 to about 200 cells per gram of body weight, and in a more preferred amount of about 5 to about 100 cells per gram of body weight.

The procedure for the encapsulating of Sertoli cells with cells that produce a biological factor is general, and the procedure will be explained in more detail with respect to Sertoli cells and islet cells, which are exemplary.

In an embodiment of step (a) of the subject method, the first gelling agent is sodium alginate. It is conventionally suspended in an aqueous solution such as a buffer or saline solution containing the islets and Sertoli cells.

By "gelling effective amount" is meant an amount of a water soluble gelling agent capable of binding calcium ions or other ions that interact with the gelling agent to form a network. More specifically, the islets and Sertoli cells in combination are preferably suspended relative to the gelling agent in a ratio of about 1:20 to 20:1 (v/v) and more preferably 1:10 to 10:1 (v/v) and most preferably about 1:10 (v/v). Preferably, the Sertoli cells and islets cells are present in a ratio of about 1:1 (v/v).

The suspension is extruded by techniques commonly used in the art. It is preferred that the suspension is extruded through an air-jet needle. In a preferred embodiment, droplets containing islets and Sertoli cells in association with the alginate are produced by extrusion (1.7 ml/min) through a 22 gauge air-jet needle (air flow 5 l/min).

In an embodiment of step (b) of the subject method, the droplets are subjected to a solution of multivalent cations, such as a solution of calcium salt, e.g., calcium halide, e.g., calcium chloride solution, which form a network within said droplet. The preferred concentration is at least about 0.5% (v/v), and more preferably at least about 1% (v/v), and most preferably ranging from about 1% (v/v) to a saturated solution. In an embodiment, the droplets fall into a beaker containing a saline solution at pH7 of calcium chloride solution, e.g., 10 ml 1.1% $CaCl_2$ in 0.9% saline at pH7. This process continues for a sufficient time until the negatively charged alginate droplets bind calcium and form calcium alginate gel.

In an embodiment of step (c) of the subject method, a membrane is formed around the product of step (b) by subjecting the encapsulated product to polymers, which polymers contain substituents reactive with the gelling agents, especially the acid groups of the gelling agent. The preferred polymers are polyamine acids such as poly-L-lysine (PLL) or polyethylenimine. In a preferred embodiment, the polymer is poly-L-lysine with a molecular weight of about 20 kd. It is preferred that the polymers coat the product of (b) by following the procedure of Goosen, et al. in Biotech. Bioeng., 27: 146–150 (1985), the contents of which is incorporated herein by reference. Without wishing to be bound, it is believed that positively charged poly-L-lysine displaces calcium ions and binds negatively charged alginate, producing a polyelectrolyte membrane.

In an embodiment of step (d) of the subject method the second gelling agent may be sodium alginate which may improve the biocompatability of the capsule in a mammal. The second gelling agent may be added according to the methods employed by Weber, et al. U.S. Pat. No. 5,227,298, incorporated herein by reference. The double walled semi-permeable capsules formulated in connection with the present invention have molecular weight cut-offs in the range of 50,000 daltons and provide sustained release of factors produced by the encapsulated islets and Sertoli cells. The capsules comprise semi-permeable membranes which function to protect islets from immune responses while simultaneously permitting passage of biological factors produced by islets into the mammal. In still another embodiment of the present invention, co-localized, e.g., co-encapsulated islets and Sertoli cells are connected to a blood supply by techniques known in the art, thereby permitting the free flow of nutrients and inhibiting the influx of molecules produced by the immune system.

The co-localized, e.g., encapsulated cells producing biological factor and Sertoli cells are effective in treating a disease resulting from a deficiency of said biological factor. For example, the co-localized, e.g., encapsulated islet cells with Sertoli cells, are effective in treating diabetes mellitus. Thus a preferred embodiment of this invention is directed to a method of treating diabetes mellitus by co-localizing, e.g., co-encapsulating and transplanting islet of Langerhans into the peritoneal space. This method not only prevents the complications of the disease process, but also reduces the adverse effects associated with other therapies. This method also provides a biological factor in appropriate amounts which are released in a physiological manner.

The present invention is also directed to a kit for treatment of a disease. In one embodiment, the kit is compartmentalized to receive a first container adapted to contain Sertoli cells in an amount effective to create an immunologically privileged site in a mammal, and a second container adapted to contain a therapeutically effective amount of cells that produce a biological factor that is absent or defective in the disease to be treated. In a preferred embodiment, the Sertoli cells are bovine, porcine or human and are provided in an amount of from $10^1$ to $10^{10}$ cells. In a more preferred embodiment, Sertoli cells are provided in an amount of from $10^5$ to $10^{10}$ cells. In another preferred embodiment the cells that produce a biological factor are cells that have been transformed with DNA encoding the factor. In yet another preferred embodiment the cells that produce the factor are pancreatic islet cells. The islet cells are provided in a preferred amount of 5 to 200 cells per gram of body weight, and in a more preferred amount of 5 to 100 cells per gram of body weight.

The present invention further provides an article of manufacture comprising a packaging material and Sertoli cells contained within said packaging material, wherein said Sertoli cells are effective for creating an immunologically privileged site in a mammal, and wherein said packaging material contains a G label that indicates that said Sertoli cells can be used for creating an immunologically privileged site in a mammal. The packaging material used to contain the Sertoli cells can comprise glass, plastic, metal or any other suitably inert material.

Unless specified to the contrary, it is to be understood that percentages are by volume.

In order to further illustrate the present invention, the experiments described in the following examples were carried out. It should be understood that the invention is not limited to the specific examples or the details described therein. The results obtained from the experiments described in the examples are shown in the accompanying figures and tables.

EXAMPLE 1

Six male Rhesus monkeys were transplanted with islet allografts in their testes to examine the survival of these transplants. The recipients were made diabetic by means of a near total pancreatectomy, followed two weeks later by an intravenous injection of 35 mg streptozotocin/kg body weight. This procedure resulted in the induction of severe diabetes melitis. Plasma glucose levels were in excess of 400 mg/dl and the animals were ketotic. Malabsorption was prevented by the oral administration of VACUOUS®, one tablet given twice daily before each meal.

Islets were isolated from female Rhesus monkeys. First, the pancreases of five animals were removed, pooled and chopped finely into smaller fragments. After collagenase digestion in a water bath at 37° C., the islets were separated from exocrine tissues and other cellular debris on at least two Ficoll gradients, prepared in tandem. The islets were washed three times by centrifugation in ice-cold Hanks's buffer and then handpicked and transferred in groups of 150 to biologic grade Petri dishes. Each dish contained 6 mL of culture medium CMRL-1066 supplemented with 5% fetal calf serum, glucose at a concentration of 250 mg/dL, penicillin (100 U/mL), and streptomycin (100 $\mu$/mL). Incubation of islets were carried out at 35° C. in 5% CO and air for 4 to 6 days. The islets were transferred to fresh medium at 48 hour intervals.

Viability and counting of the islets were facilitated by means of the uptake of the dye dithizone. Each monkey received an average of about $10^4$ islets/kg body weight injected into both testes. In the first three animals the testes were elevated into the abdominal cavity, whereas in the last three recipients the grafted organs were anchored into the inguinal canal. Cyclosporine (CsA) was administered, in varying doses to the first three grafted animals over a 30 day period, whereas the last three hosts were given 7 injections of CsA (20 mg/kg) on days −4 to +3. Oral sustacal tolerance tests were done on day 30, and then at intervals in the normoglycemic animals, as follows.

The monkeys were housed individually in cages and given standard monkey chow and fruit twice daily. In addition, a pancreatic enzyme was mixed with the food since the monkeys had been pancreatectomized to make them diabetic before transplantation.

The night before the test, the animals were fasted for 12 hours. At 8 a.m. the next morning they were then anesthetized and prepared for the test meal. Sustacal was used as the test agent. Sustacal consists of a physiologic mixture of carbohydrates, proteins and fat which closely mimics a standard meal and which is a powerful stimulus for the release of insulin.

Sustacal was injected directly into the stomach of the sleeping animal through a nasogastric tube. Blood samples were then obtained at times 0, 15, 30, 60, 90, 120 and 180 minutes. The samples were centrifuged and the serum stored at −20° C. until measurements for insulin or C-peptide could be carried out. C-peptide is a very sensitive marker for beta cell function. The results are shown in FIGS. 1–4.

FIG. 1 shows the glucose responses to oral sustacal tolerance tests done on the monkey "Lucky" at intervals before pancreatectomy (Lucky-pre); after pancreatectomy but prior to transplantation (Lucky-post); and at intervals following transplantation (143 days, 730 days and 930 days, respectively).

It can be readily appreciated that the animal became severely diabetic after the removal of his pancreas (Lucky-post). Following transplantation the glucose responses were restored to normal levels at all of the time intervals measured (143, 730 and 930 days following transplantation). Lucky showed no evidence of graft failure. With graft failure glucose levels would become elevated would approach those which were found following his pancreatectomy.

Figure 2:
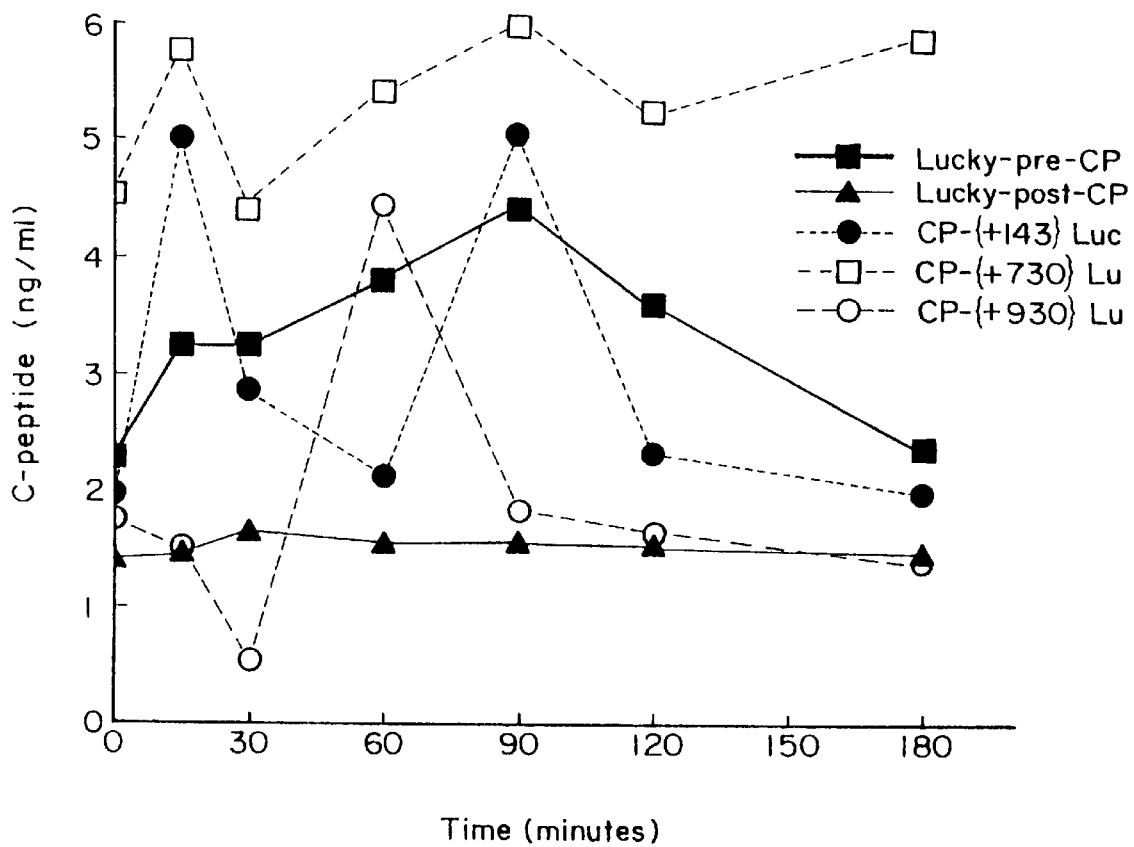
FIG. 2 shows the C-peptide responses to an oral sustacal tolerance test at the same time intervals as depicted in FIG. 1.

FIG. 2 shows the C-peptide responses to an oral sustacal tolerance test at the same time intervals as depicted in FIG. 1. Following his pancreatectomy the C-peptide responses became blunted indicating a severe diabetes. But following transplantation the levels were not only restored to normal but appeared to show a hyperresponsive pattern of C-peptide release and levels done on day 730 exceed the normal levels at all points measured. The elevated levels might be due to the fact that insulin released from the testis enters the systemic circulation. By contrast, insulin released from the pancreas enters the portal vein and travels immediately to the liver where about 60% is broken down during the first passage. Insulin released into the systemic circulation reaches the liver much later, thus the elevated levels. As was evident with an investigation of the glucose concentrations, the C—peptide responses showed no evidence of failure 30 months following transplantation.

Figure 3:
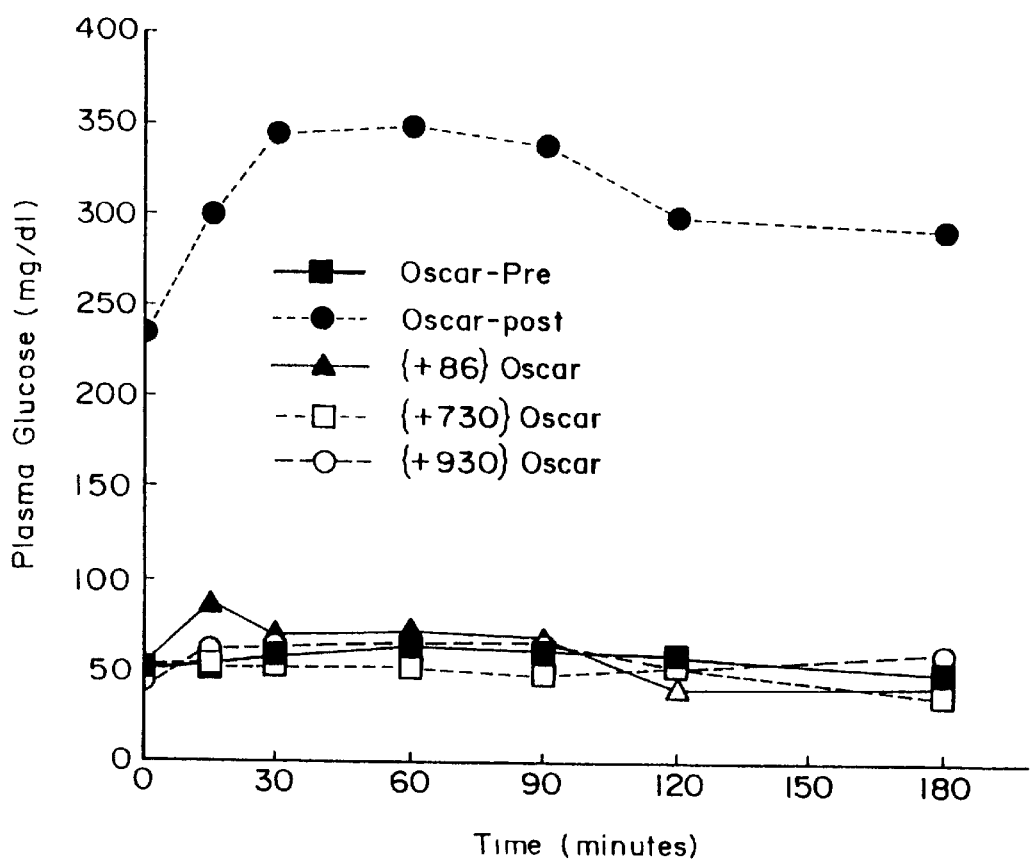
FIG. 3 shows the glucose responses to oral sustacal tolerance tests in the monkey "Oscar".

FIG. 3 shows the glucose responses to oral sustacal tolerance tests in the monkey "Oscar". Following the removal of his pancreas he became severely diabetic with elevated glucose levels. Following transplantation of islets the glucose responses became similar to those determined before his pancreas was removed. The glucose levels remain within normal levels 32 months following transplantation.

Figure 4:
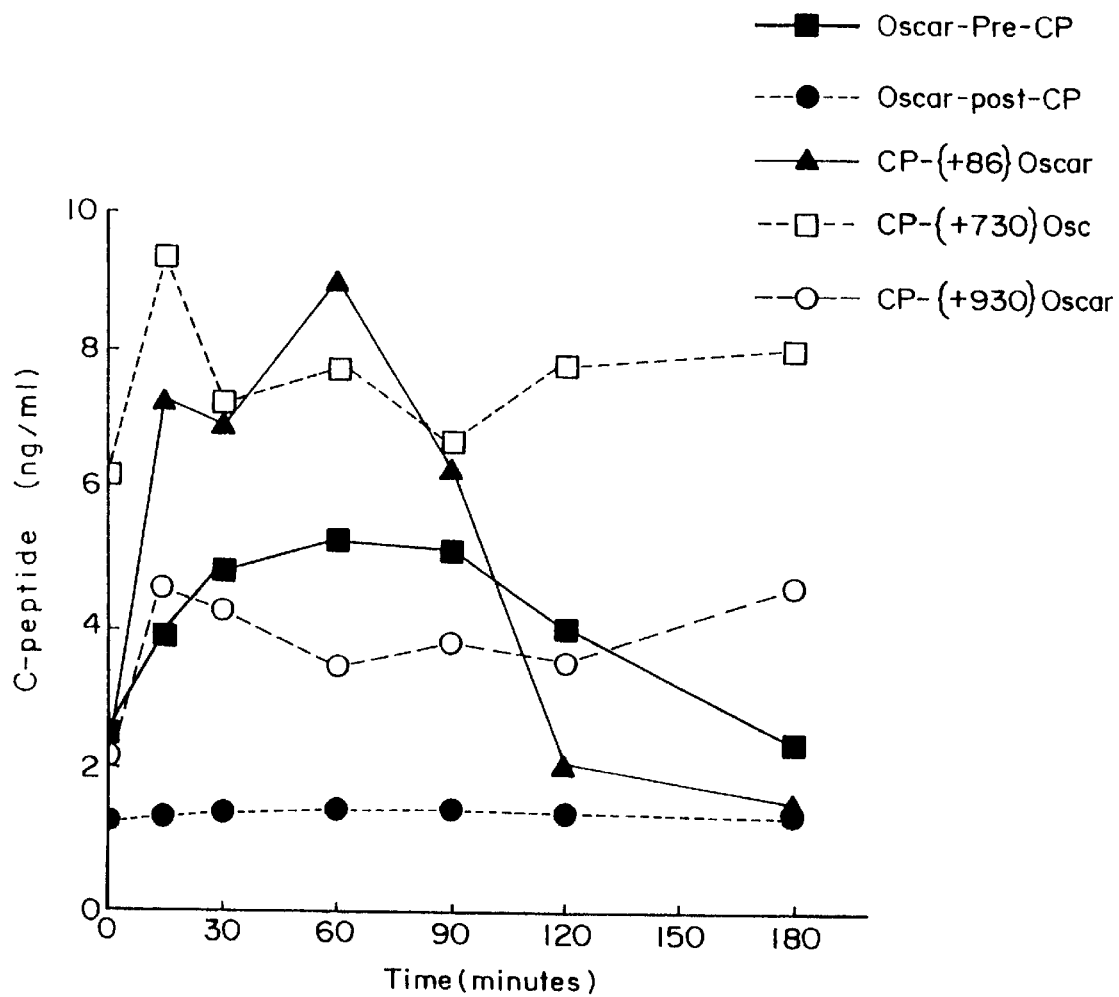
FIG. 4 shows the C-peptide responses in the same animal and at the same intervals depicted for FIG. 3.

FIG. 4 shows the C-peptide responses in the same animal and at the same intervals depicted for FIG. 3. The animal became very diabetic following the removal of his pancreas and shows blunted C-peptide responses as a result. Following transplantation and for the next 730 days the C-peptide responses were greater compared with the normals. on day 930 following transplantation the C-peptide responses have become somewhat less compared with the normals. Despite somewhat lower C-peptide levels the animal remains normoglycemic.

This example demonstrates that primates can be successfully transplanted with intratesticular islet allografts without the need for sustained immunosuppression, and that functional integrity of intratesticular islet allografts is maintained for periods exceeding two years with no evidence of graft failure.

EXAMPLE 2

This study examined insulin and glucagon secretory patterns in spontaneously diabetic bb/Wor dp rats transplanted with abdominal, intratesticular, islet grafts. Diabetic, BB/Wor dp, rats received intratesticular islet grafts from MHC-compatible BB/Wor dr rats and no immunosuppression. After a period of 74±15 days, of normoglycemia, three different groups (controls; BB/Wor dp, transplanted; and BB/Wor dp, insulin treated) were given the following challenges; (1) an oral glucose tolerance test (OGTT), (2) a single oral dose of glipizide, followed by an OGTT, and (3) arginine, by intravenous infusion. The results of this study are shown in Tables 1 and 2 and FIGS. 5 and 6.

TABLE 1

Metabolic Parameters and Immunoreactive Serum Insulin and Glucagon Levels in Control and in Transplanted and Insulin Treated BB/Wor dp Rats

| | BB/Wor dp | | |
|---|---|---|---|
| | CONTROLS | GRAFTED* | INSULIN TREATED |
| Plasma Glucose (mg/dl): Prior to Therapy | 112 ± 5 | 502 ± 8+ | 510 ± 13+ |
| After 2.5 months | 97 ± 4 | 110 ± 3 | 350 ± 40# |
| Duration p.t. OGTT (days) | 75 ± 6 | 70 ± 11 | 78 ± 19 |
| Weight Gain (g) | 120 ± 6 | 105 ± 17 | 48 ± 14$ |
| Fasting Plasma Insulin (uU/ml) | 21.9 ± 3 | 20.4 ± 2 | ND |
| Fasting Plasma Glucagon (pg/ml) | 37.8 ± 5.7 | 43.4 ± 4.6 | 47.4 ± 4.9 |

*Duration of normoglycemia after grafting (days) = 279 ± 25
+P < 0.0001 vs. control
P < 0.0001 vs. grafted
$P < 0.02 vs. grafted

TABLE 2

Pancreatic and Testicular Insulin and Glucagon Content in Control and in Transplanted and Insulin Treated BB/Wor dp Rats

| | BB/Wor dp | | |
|---|---|---|---|
| | CONTROLS | GRAFTED | INSULIN TREATED |
| Pancreas (mg) | 1573 ± 171 | 757 ± 122 | 920 ± 32 |
| Insulin (ug/g) | 66 ± 5.03 | 0.58 ± 0.18 | 0.76 ± 0.12 |
| Glucagon (ng/mg) | 4.1 ± 0.35* | 49. ± 0.33** | 6.9 ± 0.08 |
| Testes Fractions: (mg) | 493 ± 49.6 | 582 ± 59.2 | 430 ± 28.0 |
| Insulin (ug/g) | 0.0 | 59.70 ± 0.49 | 0.0 |
| Glucagon (ng/mg) | 0.0 | 1.4 ± 0.37 | 0.0 |

*P < 0.03
**P < 0.08 vs. diabetic, respectively

Figure 5B:
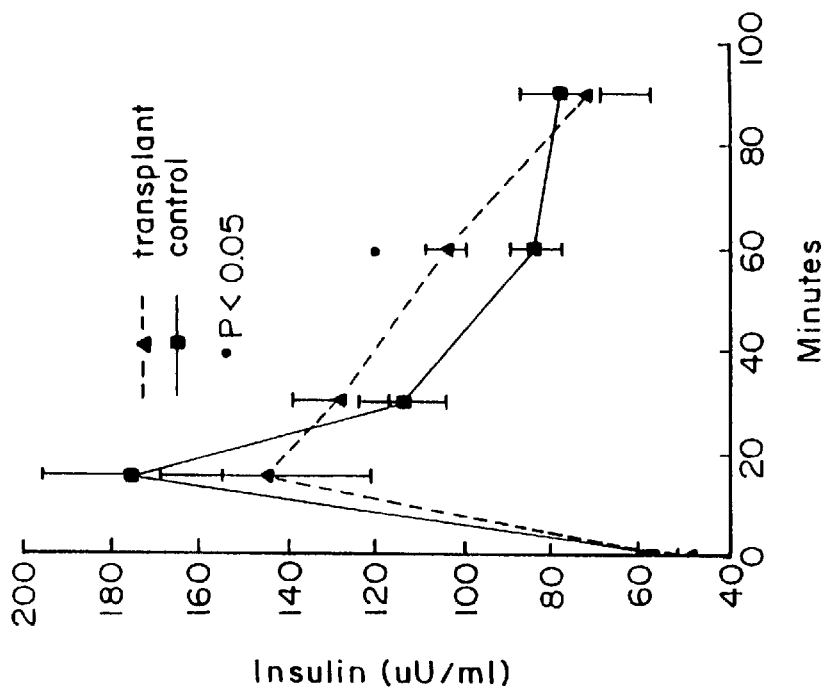
FIGS. 5a and 5b show the effect of intratesticular islet allografts on serum glucose levels and the insulin responses to oral glucose in spontaneously diabetic BB/Wor dp rats.
Figure 5A:
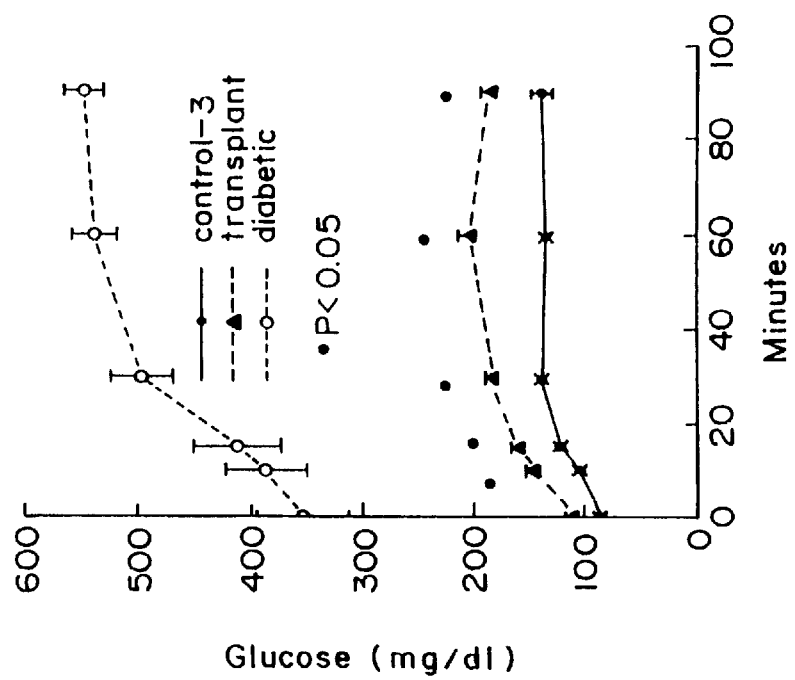

FIG. 5 shows the effect of intratesticular islet allografts on serum glucose and insulin responses to oral glucose in spontaneously diabetic BB/Wor dp rats. FIG. 6 shows the effect of intratesticular islet allografts on plasma glucagon secretory responses to oral glucose and a combination of glucose plus glipizide in spontaneously diabetic BB/Wor dp rats. This experiment demonstrates that grafted testes in spontaneously diabetic BB/Wor dp rats contain both alpha and beta cells, and that the alpha and beta cells have the capacity to respond to specific secretagogues independently.

EXAMPLE 3

This study investigated the effect of Sertoli cell enriched fraction (SEF) on islet allograft survival in the renal subcapsular space of diabetic rats.

The animals used in this study were PVG rats, weighing between 150–200 g. Diabetes was induced by means of a single intravenous injection of 65 mg/dL of streptozotocin. Only rats with plasma glucose levels in excess of 400 mg/dL were transplanted. Sprague Dawley (S-D) outbred rats were used as islet donors. Either PVG or S-D male rats between 16 and 18 days old were used as Sertoli cell donors.

Islet Preparation

Islets were prepared according to modification of the method of London et al. (1990) *Transplantation,* 49: 1109–1113. The islets were purified on Ficoll gradients, and the isolated cells were then incubated for 4 days at 37° C. in a humidified atmosphere of 5% $CO_2$, and air prior to use. No special efforts were made to deplete the islets of contaminating passenger leukocytes.

Sertoli Cell-enriched Fraction Preparation

Highly purified preparations of Sertoli cells were isolated form the testes of young males according to the method of Cheng et al. *J. Biol. Chem.*, 26:12768–12779. The testes were removed, chopped into several pieces, and placed in a 50 mL conical tube containing 50 mL of Ham's F12/DMEM media. The pieces were washed once by centrifugation at 800× g for 2 min. The supernatant was aspirated, and the tissue resuspended in 40 mL of media containing 40 mg trypsin and 0.8 mg DNase in a sterile 250 mL Erlenmeyer flask. The flask was placed in 37° C. oscillating incubator at 60–90 osc/min for 30 min. This step removed Leydig cells. The tubules were then transferred to a 50 mL conical tube, and centrifuged at 800× g for 2 min. The supernatant fraction was aspirated, and the pellet resuspended in 40 mL of 1 M glycine, 2 mM EDTA containing 0.01% soy bean trypsin inhibitor and 0.8 mg DNase, and incubated at room temperature for 10 min. This step lysed any residual Leydig cells. The cells were washed by centrifugation for 2 min, and the step repeated twice, or until the media was no longer cloudy. The pellet was resuspended by gentle homogenization with a glass Pasteur pipet in 40 mL of media containing 20 mg collagenase in an Erlenmeyer flask, and incubated at 37° C. for 5 min with 60–90 osc/min. The cell suspension was centrifuged at 800× g for two min, and the pellet resuspended by gentle homogenization with a Pasteur pipet in 40 mL media containing 40 mg collagenase and 0.2 mg DNase, and incubated in an Erlenmeyer flask at 37° C. for 30 min with 60–90 osc/min. The cells were then washed by centrifugation for 2 min, and the process repeated at least three times to eliminate peritubular cells. The, cells were resuspended by gentle homogenization with a Pasteur pipet in 40 mL media containing 40 mg hyaluronidase and 0.2 mg of DNase, and incubated at 37° C. for 30 min with 60–90 osc/min. The cells were pelleted by soft centrifugation for 2 min, and washed at least five times to eliminate germ cells. The resultant SEF was resuspended in 0.25 mL of media, and immediately transplanted into the recipient rat. Each grafted rat received the equivalent of the total amount of Sertoli cells contained in a single testis.

Transplantation of Rats

The diabetic rat was anesthetized with methoxyflurane USP in a sterile hood and the left flank opened to expose the kidney. The Sertoli-enriched fraction containing approximately 5 million Sertoli cells was injected first underneath the renal capsule. The cells could be seen as a milkish bubble underneath the capsule. Immediately afterwards, a total of 10 islets/g of body weight was injected to the same milkish bubble. The needle was retracted slowly to prevent leakage of the grafted cells. Cyclosporine (CsA) was administered subcutaneously in varying doses over a 20-day period to groups two and four. Because the grafted rats responded similarly whether the drug was administered over a 20-day, or over a 3-day period, all of the subsequent groups, including the female rats, were treated with only three injections of 25 mg/kg CsA, given on days 0, +1, and +2, relative to the graft. The rats received no other therapy.

A total of 36 male and 21 female PVG rats were divider into six different treatment groups: Group 1, the control group, consisted of 6 male rats grafted with only islets from S-D donor rats. They received neither SEF nor CsA. Group 2 consisted of 10 rats grafted with a combination of islets from S-D rats and CsA postransplantation, but no SEF. Group 3 consisted of a total of 10 rats grafted with a combination of islets from S-D and SEF from PVG donor rats, but no CsA postransplantation. Group 4 consisted of 10 rats grafted with a combination of islets from S-D donors, SEF from PVG donors, and CsA postransplantation. Group 5 consisted of 11 female rats grafted with the same combination of cells as depicted for Group four. Group 6 consisted of 10 female rats grafted with a combination of islets and SEF, both cell types from S-D donors, and CsA postransplantation.

Posttransplantation Evaluation of Rats

The grafted rats were transferred to metabolic cages, and plasma glucose levels were obtained at weekly intervals. Urine volumes and urine glucose contents were obtained at daily intervals. A rat was considered cured of the diabetic process if the following criteria were met: A random plasma glucose level $\leq 150$ mg/DL; glycosuria; and immediate reversal to hyperglycemia following surgical removal of the grafted kidney.

To determine if any of the rats had become unresponsive to their grafts, normoglycemic rats were challenged with a secondary islet allograft consisting of at least 500, freshly prepared, Sprague Dawley islets which were injected into the contralateral renal subcapsular space. No immunosuppression was given following the challenge.

To examine the impact of the transplantation of SEF on fertility of the female rats, normoglycemic animals of longer than 30 days were mated with PVG males. Metabolic parameters, as outlined above, were closely monitored, as was the course of their pregnancies.

Structural Analysis of Grafted Tissue

A total of five successfully grafted rats were nephrectomized at intervals following transplantation. Wedge sections of renal tissue, obtained from sites at which islets and SEF had been injected, were prepared for examination by light and electron microscopy, as previously described by Cameron et al. (1990) *Transplantation*, 50:649–653. Briefly, the tissue wedges were immersion-fixed with 5% glutaraldehyde in 0.1 M collidine buffer for 1 h, washed in buffer, and postfixed for 1 h with 1% osmium tetroxide in 0.1 M buffer. Small tissue blocks were cut from the wedges, and dehydrated through a graded series of ethyl alcohols, transferred to propylene oxide, and embedded in Epon 812/Araldite plastic resin. Thick (0.5 $\mu$m and thin (900 mg) sections were strained routinely with toluidine blue and uranil acetate/lead citrate, respectively, for structural analysis by light and electron microscopy. The results are shown in Table 3 and FIGS. 7–9.

TABLE 3

Effect of Sertoli Cells on Islet Allograft Survival in the Non-Immunologically Privileged Renal, Subcapsular Site

| Group (n) | Gender | Sertoli Cell (donor origin) | CsA | Duration of Normoglycemia (days) Individual Responses |
|---|---|---|---|---|
| 1 (6) | Male | — | − | 0, 0, 0, 0, 0, 0 |
| 2 (10) | Male | — | + | 0, 0, 0, 0, 0, 0, 0, 130 > 441, >445 |
| 3 (10) | Male | +(PVG) | − | 0, 0, 0, 0, 9, 10, 12, 13, 13, 14 |
| 4 (10) | Male | +(PVG) | + | 19, 76, 58*, 84*, 167*, 127†, 139†, >418†, >422†, >425† |
| 5 (11) | Female | +(PVG) | + | 7, 11, 14, 28, >287†, >305†, >306†, >308†, >441†, >447†, >457† |
| 6 (10) | Female | +(S-D) | + | 8, 10, 96*, 128*, >168, >172, >184, >193, >193, >196 |

TABLE 3-continued

Effect of Sertoli Cells on
Islet Allograft Survival in the
Non-Immunologically Privileged Renal, Subcapsular Site

| Group (n) | Gender | Sertoli Cell (donor origin) | CsA | Duration of Normoglycemia (days) Individual Responses |
|---|---|---|---|---|

*Nephrectomized
†Challenged with a Secondary Islet Allograft

Group 1: None of the six rats grafted with islets alone, without either SEF or CsA, became normoglycemic.

Group 2: Three of 10 rats grafted with islets and treated with CsA became normoglycemic for more than 100 days. The 3 normoglycemic rats were challenged with a secondary graft on days 116, 192 and 197, respectively. One rat reverted to hyperglycemia on day 130, while 2 remained normoglycemic.

Group 3: Initially 6 of the 10 rats grafted with islets and SEF, but no CsA, became normoglycemic, but all of them reverted to hyperglycemia by day 14.

Group 4: All 10 of rats grafted with a combination of SEF and islets, and also given CsA became normoglycemic. Two reverted spontaneously to diabetes on days 19 and 76, respectively. Three were nephrectomized on days 58, 84 and 167 following transplantation. All 3 of these rats became hyperglycemic within the next 24 h. The remaining 5 rats were challenged with a secondary islet allograft on days 119, 129, 280 342 and 400, respectively. Of these, the first 2 reverted to diabetes on day 127 and 139, respectively, while the latter 3 remained normoglycemic.

Group 5: All 11 of the female rats grafted with a combination of islets and SEF, and then given CsA, became normoglycemic. of these, 4 reverted spontaneously to hyperglycemia by day 28. Of the 7 normoglycemic rats who were mated with male PVG rats, 6 became pregnant, and of these, 8 had litters varying between 1 and 10 pups. They were able to nurse the pups successfully. A total of 7 of the long-term surviving females were challenged with secondary islet allografts at least 200 days following transplantation. None of them reverted to hyperglycemia.

Group 6: of the 10 rats grafted with islets and SEF from the same donor strain of rat, all 10 became normoglycemic. Two reverted to hyperglycemia by day 10. A nephrectomy to remove the graft was done on 2 of the long-term surviving rats on days 96 and 201, respectively. Both reverted to hyperglycemic immediately within the next 24 h.

Tissue Morphology

Figure 7:
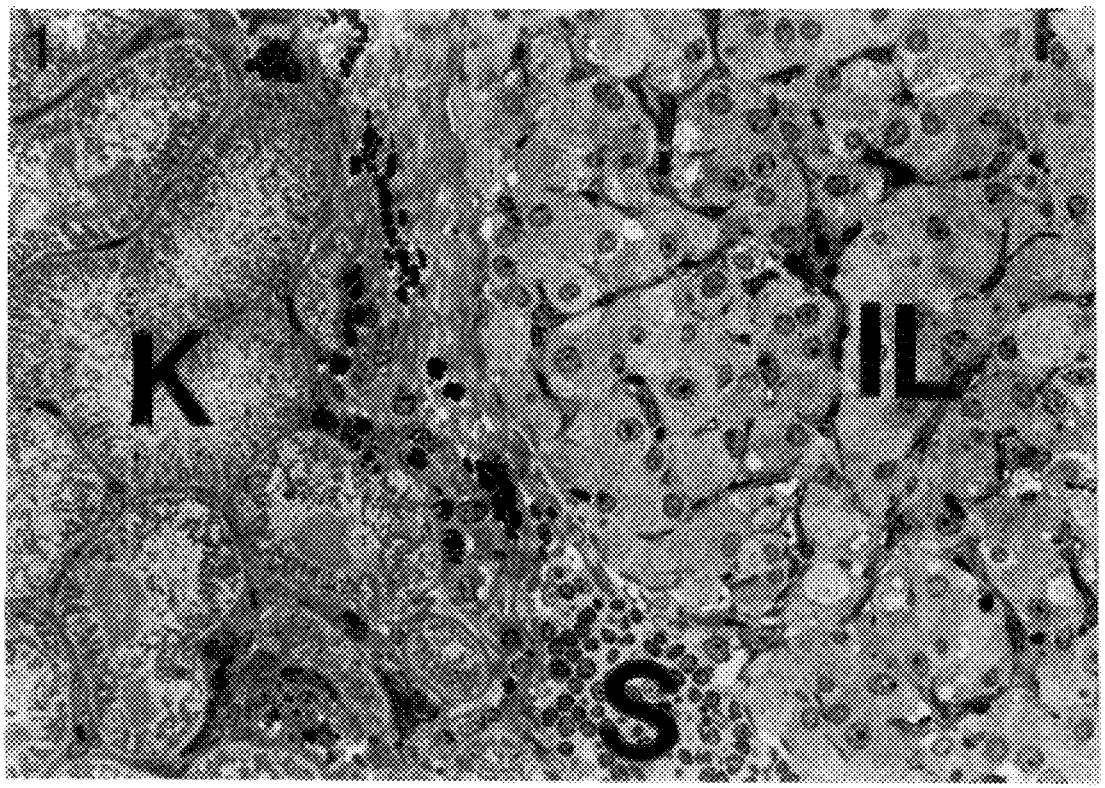
FIG. 7 shows a light micrograph of the pancreatic islets of Langerhans and the isolated rat Sertoli cells transplanted into the renal subcapsular space of a diabetic rat.
Figure 8:
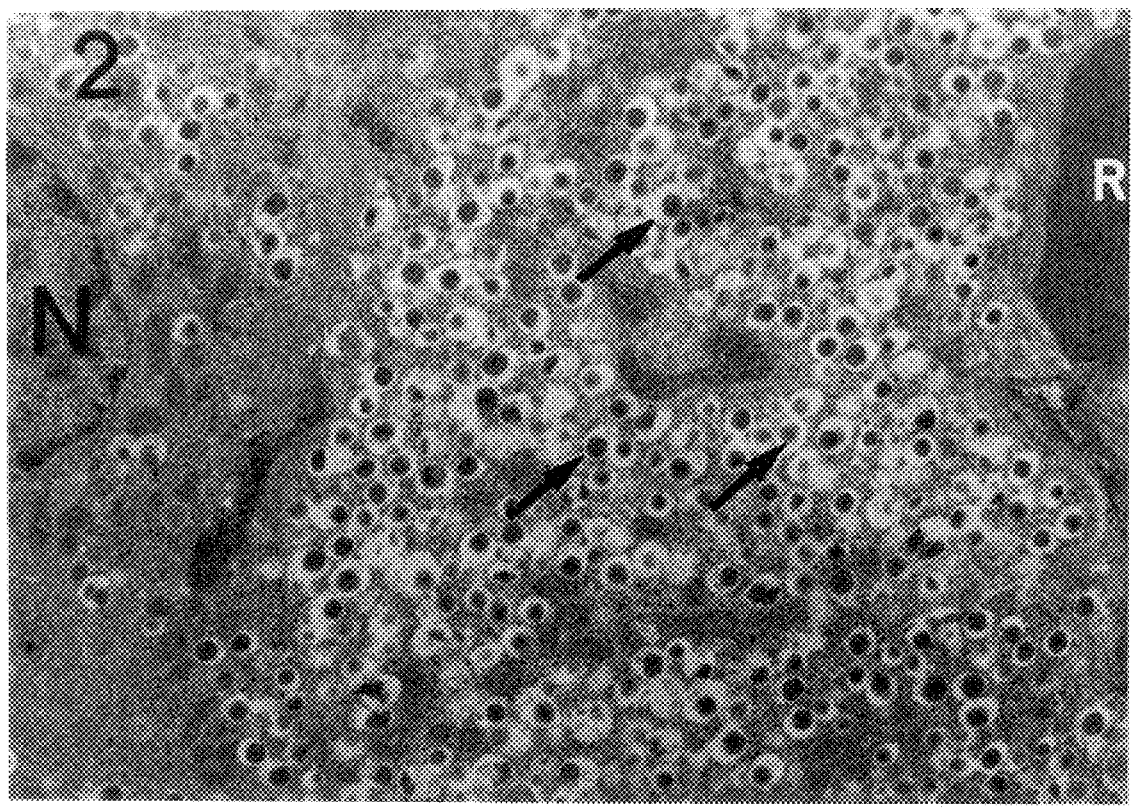
FIG. 8 shows an electron micrograph of an individual cell within the transplanted islet.

Renal tissue obtained from the long-term grafted kidney appeared structurally normal by light microscopy (FIG. 7). Transplanted islets in this organ were immediately subjacent to the kidney capsule, and also appeared structurally normal. They displayed tissue and cellular architecture identical to islets in situ (FIG. 7). Individual islet cells were partitioned into cell clusters by thin connective septa containing small vessels and capillaries (FIG. 7). It appeared that most of the islet cells contained secretion granules. When resolved by electron microscopy, islet cells were identified as the P-cell type by the inclusion of ultrastructurally distinctive, and unique insulin-containing secretion granules (FIG. 8). All β-cell clusters observed were in close proximity to intra-islet capillaries (FIG. 8).

Figure 9:
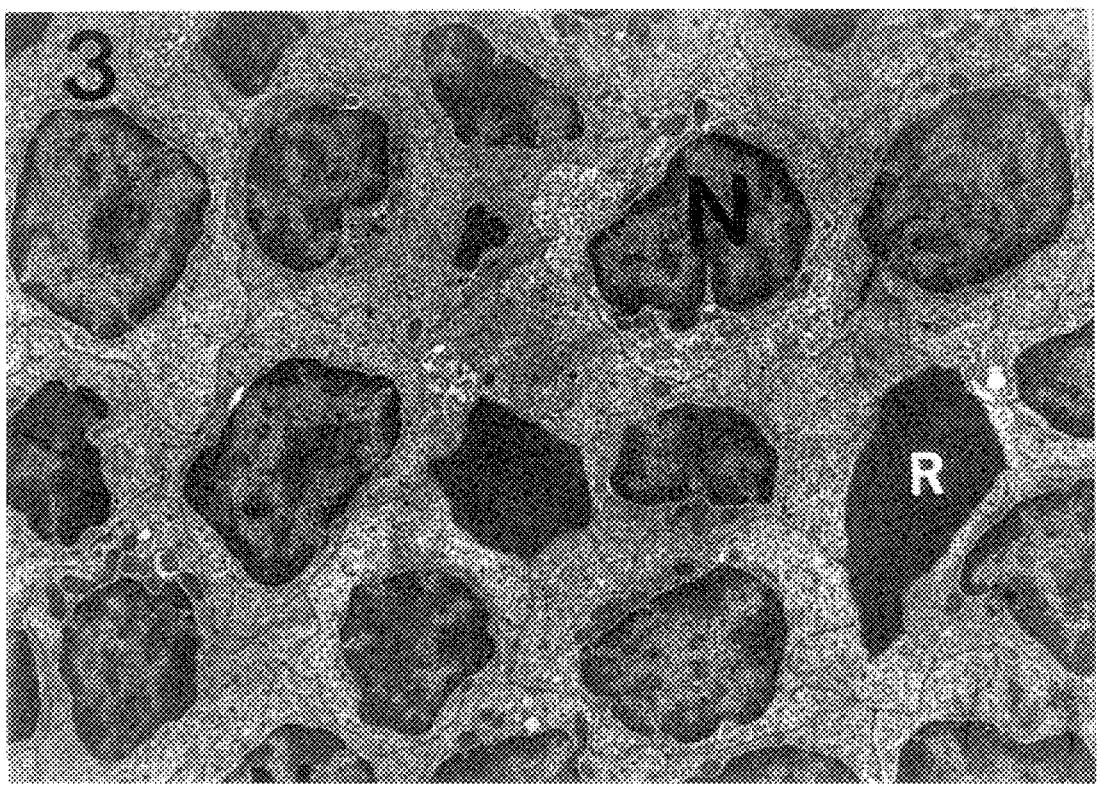
FIG. 9 shows an electron micrograph of the fine structure of the extra-islet cells labeled "S" in FIG. 7.

There was a high density of cells between, and directly adjacent to, the transplanted islets and renal parenchyma. By light microscopy, they did not appear to be islet cells, kidney cells nor cells or blood origin (FIG. 7). When observed by electron microscopy, these cells were similar in ultrastructure to Sertoli cells in that their nucleic were irregular in profile, and contained deep nuclear clefts, distinctive nucleoli were often present, and mitochondrial structure was dense. Although these cells did not retain the typical polarity of Sertoli cells in vivo, they were, however, identical in appearance to Sertoli cells in vitro, when the cells are not plated on a basement membrane substrate. The cells were not associated with a basement membrane, and appeared randomly organized (FIG. 9). Cells showing ultrastructural features of either germ or Leydig cells were not observed.

This example demonstrates that an immunologically privileged site for transplantation of isolated islet can be created in male and female diabetic recipients by transplantation of Sertoli cells without the need for sustained immunosuppression.

EXAMPLE 4

This study determined the survival of discordant islet xenografts in various nonimmunologically privileged organ sites in experimental animals.

Islets were prepared from young piglets as follows: Male piglets not weighing more than 2.2 kg were used exclusively. The piglet was anesthetized and following exsanguination both pancreas and testes were harvested under sterile conditions. A collagenase solution consisting of 2 mg/ml of collagenase type XI (Sigma) was injected directly into the pancreas. The pancreas was incubated at 37° C. for 17 minutes and the digested tissues washed three times by means of centrifugation and aliquots of 1 ml each transferred to Petri dishes. The islets were incubated at 32° C. in tissue culture media 199 supplemented with 10% horse serum for six days.

On day seven the cultured islets were collected in batches of ±4,000 and cryopreserved using a standard protocol. The cells were stored in liquid nitrogen at 96° C. for periods varying between two and four weeks. The islets were removed from the liquid nitrogen and thawed using an established procedure. The thawed islets were transferred to Petri dishes and co-cultured with pig Sertoli cells for three days at 32° C. in the same 199 culture media as described above. Earlier studies have shown an improved survival rate of thawed islets cultured in the presence of Sertoli cells.

On day three following thawing the islets were hand-picked and counted and a total amount of 12 islets/g of body weight transplanted into female diabetic Sprague Dawley rats. A total of 5 million Sertoli cells procured from the piglet testes were grafted simultaneously into the same location. The organ sites to be tested for the grafting of islets include: a] the renal subcapsular space, b] subcutaneously, and c] the liver. Following transplantation, the rats were treated with cyclosporine as follows: 25 mg/kg for 7 days: 15 mg/kg for 5 days; 10 mg/kg for 5 days; 5 mg/kg for an additional 13 days. On day 30 the drug was discontinued.

To demonstrate viability and functional integrity of isolated piglet islets the following studies were done: a) staining of Cells with dithizone, a stain is highly specific for insulin; b) staining of cells with 0.4% trypan blue which indicates viability of the islets; and c) culturing of batches of 5 islets in the presence of insulin secretagogues such as low and high glucose concentrations at specified intervals following culturing, cryopreservation and thawing. The results are shown in Table 4.

TABLE 4

Insulin Secretion (micro-units/ml) from
Incubated and from Cryopreserved-Thawed Islets
Done on Days 3, 7 and 14 of Culturing, Respectively

|  | 3 DAYS | 7 DAYS | 14 DAYS |
|---|---|---|---|
| INCUBATED ISLETS PRIOR TO CRYOPRESERVATION: | | | |
| a) Low Glucose (90 mg/dl) | 15.3 ± 3.8 | 21.8 ± 1.1 | 17.29 ± 2.4 |
| b) High Glucose (300 mg/dl) | 32.2 ± 5.4 | 37.14 ± 3.4 | 23.3 ± 1.8 |
| CRYOPRESERVED AND THAWED ISLETS: | | | |
| a) Low Glucose (90 mg/dl) | 14.52 ± 2.8 | 7.13 ± 1.3 | 5.38 ± 2.02 |
| b) Low Glucose + Sertoli Cells | 10.31 ± 2.8 | 9.17 ± 2.6 | 8.38 ± .41 |

TABLE 5

Yield of Porcine Islets Following 1, 3 and 7 Days of Culture
and the Percentage of Islets Lost During 7 Days of Culture

| Pig. No. | BW (kg) | Panc. W g | D1 Islets/ g panc. | D3 Islets/ g panc. | D7 Islets/ g panc. | Islet Loss % D7/D1 |
|---|---|---|---|---|---|---|
| 1 | 1.6 | 1.79 | 36,536 | 31,659 | 27,212 | 26% |
| 2 | 2.0 | 1.89 | 37,272 | 32,962 | 27,883 | 25% |
| 3 | 2.3 | 2.46 | 29,268 | 26,046 | 20,884 | 29% |
| 4 | 1.8 | 1.66 | 39,904 | 37,726 | 31,664 | 21% |
| 5 | 1.8 | 1.76 | 37,846 | 34,578 | 30,046 | 21% |
| 6 | 1.6 | 1.74 | 39,866 | 37,888 | 32,424 | 19% |
| 7 | 1.4 | 1.61 | 42,126 | 39,456 | 33,872 | 20% |
| 8 | 2.3 | 2.48 | 33,682 | 29,334 | 24,892 | 26% |
| 9 | 2.1 | 2.28 | 43,478 | 41,226 | 37,394 | 14% |
| 10 | 2.1 | 2.09 | 40,126 | 36,448 | 33,282 | 17% |
| 11 | 2.1 | 2.12 | 31,248 | 27,170 | 26,415 | 15% |
| 12 | 2.1 | 1.98 | 38,848 | 36,465 | 29,293 | 25% |
| 13 | 2.2 | 2.06 | 39,146 | 37,446 | 31,709 | 19% |
| 14 | 2.2 | 2.24 | 27,892 | 25,028 | 21,342 | 23% |
| 15 | 2.7 | 2.69 | 44,610 | 38,364 | 31,524 | 29% |
| 16 | 1.5 | 1.44 | 42,222 | 40,414 | 31,244 | 26% |
| Mean ± SE | 2.0 ± 0.3 | 2.0 ± 0.4 | 37692 ± 1233 | 34513 ± 1307 | 29442 ± 1119 | 22.2 ± 1.2% |

TABLE 6

Recovery of Islets Following Freezing and Thawing in Presence and Absence of Sertoli Cells

| | Islets alone | | | Islets + Sertoli cells | | |
|---|---|---|---|---|---|---|
| No. of islets | Pre-cryo | Post thawing | Recovery (%) | Pre-cryo | Post thawing | Recovery (%) |
| D3F/D3T | 250 | 152 | 61% | 290 | 212 | 73% |
| | 230 | 131 | 57% | 260 | 228 | 88% |
| | 440 | 278 | 63% | 430 | 280 | 88% |
| | 420 | 366 | 87% | 410 | 324 | 79% |
| | 450 | 290 | 64% | 440 | 358 | 81% |
| Means | | | 66.4% | | | 81.8% |
| D7F/D3T | 260 | 136 | 52% | 250 | 229 | 92% |
| | 300 | 208 | 69% | 300 | 202 | 67% |
| | 280 | 177 | 53% | 290 | 238 | 82% |
| | 360 | 205 | 57% | 350 | 300 | 86% |
| | 320 | 218 | 68% | 390 | 289 | 74% |
| | 380 | 217 | 57% | 320 | 270 | 84% |
| Means | | | 61.0% | | | 80.8% |

As shown in Table 5, the yield of islets per gram pancreas was 37692±1233, 34513±1307 and 29,442±1119, after 1, 3 and 7 days of culture, respectively. Following cryopreservation and thawing and reculturing of the cells in the presence of Sertoli cells approximately 20% of the cells were damaged or lost as shown in Table 6. Thus ±24,000 islets/gram of piglet pancreas were available for transplant purposes after cryopreservation and thawing.

The results showed that insulin secretion was blunted when glucose was used as insulin secretagogue prior to cryopreservation. The effect was more evident following cryopreservation and thawing. While the presence of Sertoli cells had marked effects on number of islets that survived cryopreservation and thawing their presence had little effect on the ability of the islets to respond to a low glucose concentration as insulin releasing agent. However, as shown in Example 8 the presence of Sertoli cells augmented the secretion of insulin in the presence of high glucose concentrations and glucose plus Forskolin.

EXAMPLE 5

Response of Diabetic Sprague Dawley Rats to the Transplantation of Islets from Piglet Donors (Discordant Xenografts)

The rats were made diabetic by means of a single i.v. injection of 55 mg/kg of streptozotocin. They were grafted only if the blood sugar was equal to or more than 400 mg/dl. Following transplantation the rats were placed individually in metabolic cages and urine volume, urine glucose content, and body weights were measured at daily intervals. Blood glucose levels were done at weekly intervals. A rat is considered cured of diabetes if the blood glucose level is 160 mg/dl or less and/or the daily urine volume is 15 ml or less.

Figure 10:
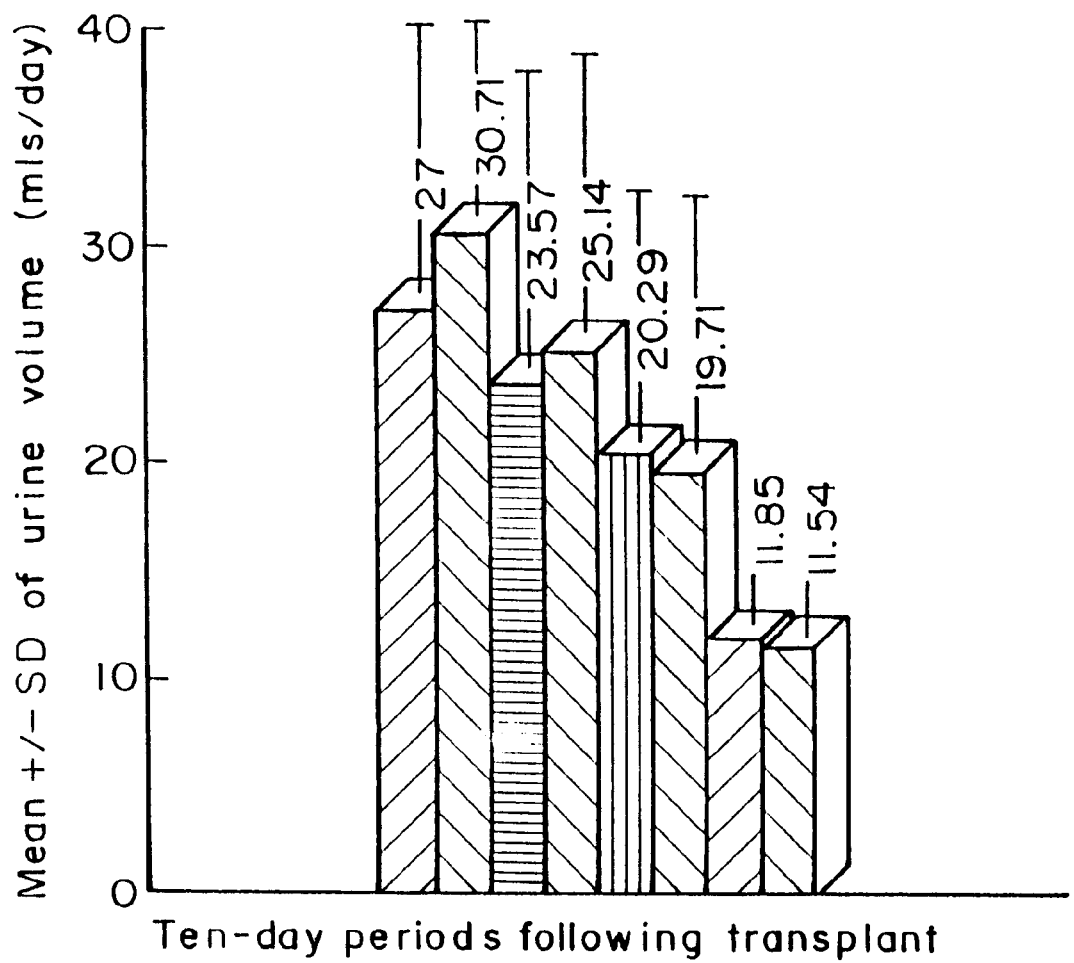
FIG. 10 shows the effect of transplantation of piglet islets and Sertoli cells underneath the renal capsule on the mean daily urine output of seven grafted female rat recipients. Each bar represents the mean daily urine output over a ten-day period following transplantation.
Figure 11:
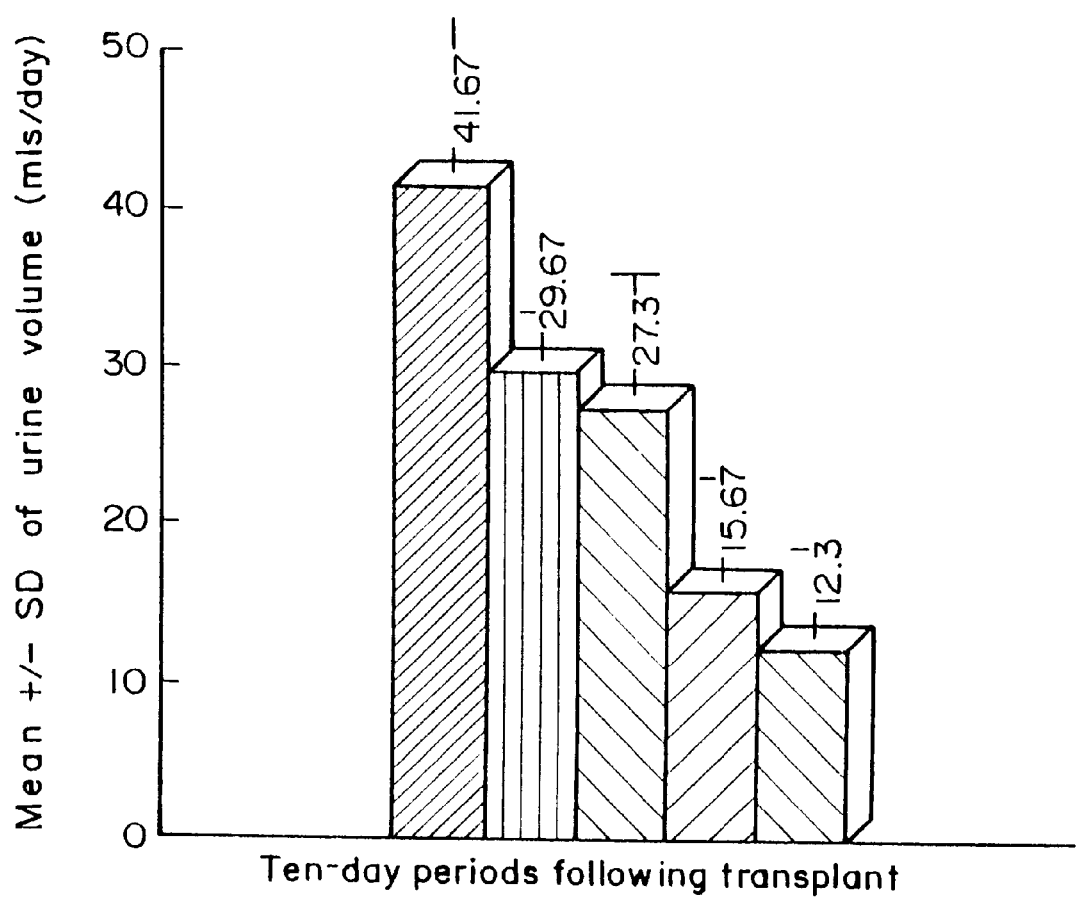
FIG. 11 shows the effect of the transplantation of piglet islets and Sertoli cells underneath the skin on the mean daily urine volumes of three rats over a 50-day period.

The results are illustrated in FIGS. 10 and 11.

FIG. 10 shows the effect of transplantation of piglet islets and Sertoli cells underneath the renal capsule on the mean daily urine output of seven grafted female rat recipients. Each bar represents the mean daily urine output over a ten-day period following transplantation. The study has been conducted over an 80-day period, the bar on the furthest right thus showing the mean urine output per day from day 80 through 89, etc.

The figure shows that the mean daily urine volume for the first 60 days varied between 19.7 mls and 27 mls or within a diabetic range. It can be readily appreciated that urine volumes decreased to near-normal levels only from days 70 through day 89. The corresponding plasma glucose levels during the first and last ten day periods were 474±46 and 155±70, mg/dl, respectively.

These results indicate that following transplantation with piglet islets and Sertoli cells the rats showed evidence of survival of the grafted islets. The reversal to normoglycemia took about 80 days.

It should be noted that one of the cured rats is pregnant and has been normoglycemic throughout her pregnancy.

FIG. 11 shows the effect of the transplantation of piglet islets and Sertoli cells underneath the skin on the mean daily urine volumes of three rats over a 50 day period. The results show that the mean urine volume decreased from a mean of 41.7 ml during the first 10-day period to an average of 12.3 mls during the fifth week. The corresponding glucose levels were 509±45, and 200±12, mg/dl, respectively.

The data depicted above demonstrate that both the renal subcapsular space and the subcutaneous area can be used as a site to create an immunologically privileged site for the transplantation of islet xenografts.

EXAMPLE 6

This study determined the effect of cultured Sertoli cells on the survival of discordant islet xenografts in diabetic rats with minimal early exogenous immunosuppression.

Preparation of Islets

Neonatal piglets of less than seven days of age were killed by anesthesia and islets were isolated according to a method of Kuo C. Y., Burghen G. A., Myvacle A. and Herrod H. G. (1994) "Isolation of islets from neonatal pig pancreatic tissue", *J. Tissue Culture Methods*, 16: 1–7. Briefly, the pancreas was distended by an injection of a collagenase solution, 2 mg/ml, collagenase type Xl, in culture medium DMEM. After incubation at 39° C. for 17 min, the digested fragments were washed by centrifugation and the digested tissue was then incubated tor one week in medium 199 supplemented with 10% horse serum and 1% antibiotics at 32° C. The islets were then cryopreserved according to the method by Lakey J. R. T., Warnock G. L., Kneteman N. M., Ao Z., Rajotte R. V. (1994) "Effects of precryopreservation culture on human islet recovery and in vitro function", *Transplant Proc.*, 26:820 and stored in liquid nitrogen at −196° C. Three days prior to transplantation the cryopreserved islets were rapidly thawed and cultured at 32° C. for two days. One day prior to transplantation some of the islets were collected and co-cultured with Sertoli cells for 24 hours.

Sertoli cell isolation

Testes of young S-D rats were removed and Sertoli cells were isolated by the method of Cheng C. Y. and Bardin C. W. (1987) "Identification of two testosteroneresponsive proteins in Sertoli cell-enriched culture medium whose secretion is suppressed by cells of the intact seminiferous tubule." *J. Biol. Chem.*, 262:12768–12779. Briefly, the testes were digested first in DMEM containing 1.0% trypsin, and then is DMEM containing 1.0% collagenase, type 1, for periods of 15 min each, at 37° C. The purified Sertoli cells were cultured at 37° C. in DMEM/Fl2 supplemented with transferrin, 10 ug/ml, FSH 10 ng/ml, insulin 20 ug/ml and 1.0% FCS, for three days. For transplantation, Sertoli cells and islets were pooled and rats were grafted with either a composite consisting of $5 \times 10^6$ Sertoli cells and 3,000 islets, or with islets alone (15 islets/g of body weight).

Transplantation of rats

Female S-D rats, weighing between 170 and 200 g were made diabetic by means of a single i.v. injection of 60 mg/kg of streptozotocin. A total of 31 diabetic rats were divided into 3 groups and grafted as follows: Group 1, a control group (n=8), received a total of 15 islets/g body weight injected underneath the renal capsule. No Sertoli cells were grafted. Following transplantation the rats were treated with cyclosporine for 55 days: 25 mg/kg for 3 days, 15 mg/kg for 10 days, 10 mg/kg for 10 days and 5 mg/kg for the following 32 days. Immunosuppression was then stopped. Each rat received, in addition, 1–3 U of Ultralente insulin at daily intervals if the 24-hour urine glucose content exceeded I g. Insulin therapy was stopped on day 55. Group 1, a tissue control group (n=8), was given a renal, subcapsular injection of a composite of about $5 \times 10^6$ Sertoli cells and 3,000 islets. No CsA was given. Insulin was given as depicted above. Group 3, the experimental group (n=15), was transplanted with both sertoli cells and islets and then treated with CsA and insulin according to the schedule outlined above.

Posttransplantation evaluation of rats

Plasma glucose levels were obtained at weekly intervals. Twenty four hour urine volumes and urine glucose contents were recorded daily. A rat was considered cured of the diabetic process if the following criteria applied: A plasma glucose level of equal to or less than 10 mmol/L, a 24-hour urine volume of less than 15 ml, and immediate reversal to hyperglycemia following surgical removal of the grafted kidney. One normoglycemic rat was mated on day 69 to test her ability to become pregnant.

Structural analysis of the grafted tissue

Two normoglycemic rats were nephrectomized on days 117 and 330 and grafted tissue prepared for light and electron microscopy. Selawry H. P., Cameron D. F. (1992) "Sertoli cell-enriched fractions in successful islet cell-transplantation", *Cell Trans.*, 2:123–129. Briefly, tissue wedges were immersion-fixed with 5% glutaraldehyde in 0.1 M collidine buffer for 1 h., washed in buffer, and postfixed for 1 h with 1% osmium tetroxide in 0.1 M buffer. Small tissue blocks were cut from the wedges, and dehydrated through a graded series of ethyl alcohols, transferred to propylene oxide, and embedded in Epon 812/Araldite plastic resin. Thick (0.5 um) and thin (900 ng) sections were stained routinely with toluidine blue and urinal acetate/lead citrate, respectively, for structural analysis by light and electron microscopy.

The results of the effect of Sertoli cells and cyclosporine on survival of xenographic transplantation of pig islet cells into the renal subcapsular space of diabetic female rats are shown in Table 7.

TABLE 7

| Group (n) | Sertoli Cells | CsA | Graft Survival (days) |
|---|---|---|---|
| 1 (8) | − | = | 0, 0, 0, 0, 0, 0, 0, 0 |
| 2 (8) | + | − | 0, 0, 0, 0, 0, 0, 0, 0 |
| 3 (15) | + | + | 0, 0, 0, 0, 0, 71, 77, 96, 117* 148#, >154, >165, >327, 330* |

*rats nephrectomized to remove the xenograft
rat died during a cardiac puncture As shown in Table 7, none of the rats grafted with islets alone and then given CsA and low-dose insulin (Group 1) became significantly less hyperglycemic. Further, none of the rats grafted with a composite of islets and Sertoli cells, but without CsA, showed any improvement of hyperglycemia (Group 2). Of 15 rats grafted with islets and Sertoli cells and then given CsA (Group 3), 10 showed evidence of reversal of the diabetic state. Four of the ten are still normoglycemic for periods of more than 154, 165, 165, and 327 days, respectively. The normoglycemic rats who were nephrectomized on days 117 and 330, became hyperglycemic immediately. Their plasma glucose levels were 4.9 mmol/L, and 8.2 mmol/L, prior to, and 20.7 mmol/L, and 32.2 mmol/L, respectively, following nephrectomy. A female rat who was mated on day 69 became pregnant and delivered a total of 10 pups on day 89, all of whom she nursed successfully while remaining normoglycemic. She died on day 148 as a result of a cardiac puncture. Three of 10 rats regressed into hyperglycemia on days 71, 77, and 96, respectively, after a short period of euglycemia.

These results demonstrate that prolonged survival of a discordant islet xenograft (pig to rat) can be achieved in female diabetic rats. Survival of islet xenografts depended upon two factors which had to be administered concomitantly: Co-transplantation with Sertoli cells and treatment with cyclosporine.

The response of total urine volumes following transplantation with a composite of pig islet and rat Sertoli cells measured at 10-day intervals over an 80 day period for 7 of the improved rats showed an average daily urine volume of 27.0±13.0 ml/rat during the first 10-day period, which slowly declined to a mean of 12.0±4.0 ml/rat, 70 days following transplantation.

Figure 12:
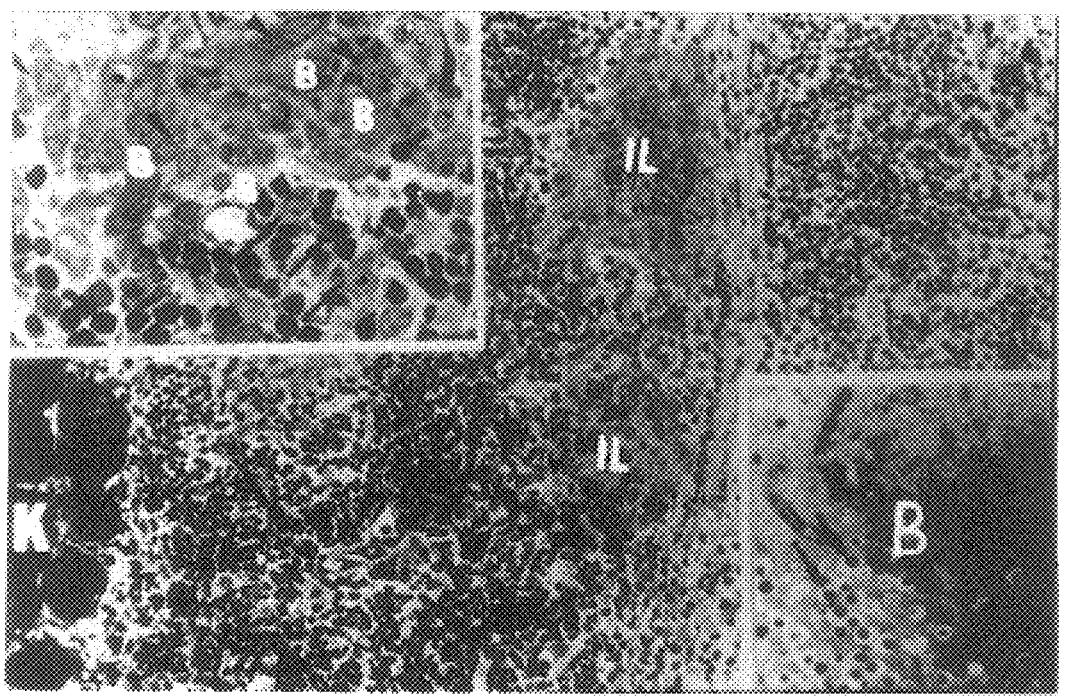
FIG. 12 shows the light photomicrograph of pig islets of Langerhans and rat Sertoli cells transplanted into the renal subcapsular space of a diabetic rat. IL shows the presence of islands of beta cells (IL) surrounded by an infiltration of small lymphocytes underneath the renal capsule (K); B (upper left) shows at higher magnification that the islands (IL) consist of beta cells and B (lower right) shows that beta cells contain characteristic insulin granules.

Tissue morphology studies shown in FIG. 12 show that the tissue and cellular structure of kidney parenchyma appeared normal in the rat nephrectomized 117 days following transplantation. Normal appearing islets with structurally distinct B-cells were visible in well vascularized areas subjacent to the kidney capsule. Additionally, normal appearing Sertoli cells were observed adjacent to the transplanted islets along with numerous lymphocytes. No plasma cells were identified at the transplantation site. Viable endocrine cells were similarly observed in the subcapsular renal space of the rat nephrectomized 330 days following transplantation.

These studies show that significant prolongation of survival of a discordant islet xenograft can be achieved without sustained immunosuppression. These studies demonstrate that the mechanism by which Sertoli cells promote islet xenograft survival is three-fold: (1) Sertoli cells stimulate the recovery of islets damaged during transplantation (i.e. improve the yield and function of cultured islets), (2) Sertoli cells protect grafted islets from immunologic rejection by producing factors which strongly suppress proliferation of T-cells, and (3) Sertoli cells protect grafted islets from the toxic effects of cyclosporine.

EXAMPLE 7

This study shows a method of isolating and cryopreserving porcine pancreatic islets for future xenographic transplants in mammals.

Male piglets, <7 days old and weighing 2±kg were used as donors. The pancreases, weighing 1.4±0.3 g, were harvested and injected with DMEM solution containing 2 mg/ml collagenase XI. The distended pancreas was incubated in a shaking water bath at 39° C. for 17 min. The digested tissue was filtered through a 500 pm stainless steal filter and filtrates were washed ×3 with cold DMEM. Without further purification the cells were cultured in M199 and 10% horse serum at 32° C. for 7 days. The islet cells were then cryopreserved using standard procedures. At specified intervals islets were thawed and cultured in M199, both in presence, and isolated from testes of male piglets according to a standard method.

To test functional capacity, islets cultured for 3 and 7 days were assessed for insulin release in static incubation. In separate experiments, effect of insulin secretagogues was tested on islets cultured with and without Sertoli cells. The results of this study are shown in Tables 8 and 9.

TABLE 8

Effect of Insulin Secretagogues, Glucose and Glucose Plus Forskolin, on Insulin Release From Incubated and Frozen/Thawed (F/T) Islets in the Presence and Absence of Pig Sertoli Cells

| | Insulin Release (uU/ml/10 islets) | | |
|---|---|---|---|
| | 3.3 mmol/L glucose | 16.7 mmol/L glucose | 16.7 mmol/L glucose +100 umol Forskolin |
| Day 3 Incubated with Sertoli cells | 42.3 ± 1.2 | 112.8 ± 17.7*# | 267.7 ± 43.0**# |
| Day 3 Incubated alone | 31.3 ± 2.1 | 57.3 ± 3.8* | 123.4 ± 15.3** |
| Day 7 Incubated with Sertoli cells | 22.9 ± 1.9 | 64.5 ± 6.4*# | 153.9 ± 14.6** |
| Day 7 Incubated alone | 21.3 ± 1.2 | 37.3 ± 6.0* | 120.3 ± 11.4** |
| Day 3 F/T with Sertoli cells | 20.6 ± 4.3 | 44.9 ± 9.9* | 77.1 ± 13.7** |
| Day 3 F/T alone | 11.7 ± 2.3 | 27.9 ± 6.6* | 54.5 ± 10.7** |

Anova Test:
*vs 3.3 mmol/L p 0.5,
**vs both 3.3 & 16.7 mmol/L P < 0.05
with Sertoli cells vs islets alone P < 0.05

TABLE 9

Effect of Sertoli cells on insulin content of incubated and
frozen-thawed piglet islets.
Insulin content (uU/10 islet(s))

|  | Islets alone | Islets & Sertoli cells |
| --- | --- | --- |
| Incubated D1 | 257.0 ± 19.6 | 391.1 ± 51.4* |
| Incubated D3 | 201.1 ± 19.1# | 400.1 ± 41.0*# |
| Incubated D7 | 179.1 ± 26.2# | 271.9 ± 39.9*# |
| Frozen D3/Thaw D3 | 52.4 ± 10.3 | 132.5 ± 35.1 |
| Frozen D7/Thaw D3 | 10.4 ± 0.9 | 35.1 ± 8.2 |

Anova*islets + Sertoli cell vs. islet alone P < 0.05

These results show that: (1) large numbers of neonatal porcine islets can be isolated by a simple method; (2) cryopreservation and thawing results in about 40% loss in number of islets in the absence of Sertoli cells and about a 20% loss in the presence of Sertoli cells ; (3) cultured islets have the ability to respond to both glucose and glucose +Forskolin as insulin secretagogues; (4) the functional capacity of the cocultured islet was enhanced two-fold in the presence of Sertoli cells; (5) following cryopreservation and thawing, islets recover more rapidly in presence of Sertoli cells and the response to both glucose and glucose+ Forskolin was enhanced two fold in the presence of Sertoli cells.

EXAMPLE 8

This example describes a method of treating genetic diabetes which is demonstrated using the animal model NOD (non-Obese Diabetic).

Genetic diabetic mice (NOD) are recipients of pancreatic islet xenografts. Diabetic mice are selected from the colony of NOD mice maintained at the University of Tennessee Medical Center. The current incidence of diabetes in this colony is 80% for females and 63% of males by 25 weeks of age. Animals are considered diabetic if they have two consecutive weekly urine glucose readings of ½%(3+) and a confirmatory plasma glucose greater than 400 mg/dl. Three to ten days before transplantation of the graft, the animals receive appropriate insulin to stabilize their health. Diabetic animals are randomly divided into two groups. All animals in these two groups receive 0.3 mg of the antiCD4 antibody, GK1.5 on days −1, 0 and 1 to initiate immunosuppression. Maintenance immunosuppression with GK1.5 cyclosporine A, FK506, cyclophosphamide, rapamycin, nicotinamide or 15-deoxyspergualin may be required.

Porcine pancreatic islets for transplantation are prepared as described in Example 6 except that they are not cryopreserved. Nicotinamide (10 mM) or IGF-1 may be added to the incubation medium prior to transplantation. Porcine sertoli cells for transplant are prepared as described in Example 6. Cyclosporine may be included in the culture medium during the first four incubation days prior to transplantation.

One group of the diabetic NOD mice receive 3,000 porcine islets in 25 µl of Hank's buffered salt solution (HBSS) under the right renal capsule followed by an injection of $2\times10^7$ pig Sertoli cells in 25 µl in HBSS under the same renal capsule. A second group of mice receive a transplant consisting of only the porcine islet cells. Animals with xenografts continue to receive daily insulin injections; the amount determined by the concentration of glucose in the animals urine and plasma. Mice with plasma glucose levels less than 250 mg/dl are considered cured and no additional insulin administered.

A majority of mice receiving porcine sertoli cells and porcine pancreatic islets attain normal urine and plasma glucose levels (xenograft acceptors). In contrast, the majority of mice receiving porcine islets alone exhibit graft failure and do not attain normal glucose levels in the urine or plasma.

EXAMPLE 9

This example shows a method of monitoring the immune response elicited against cellular transplants.

Total spleen leukocytes are isolated from mice by methods known in the art from mice that have rejected their porcine islet xenografts. In preliminary experiments these leukocytes are administered to NOD/scid mice (NOD mice that in addition have genetic immunodeficiency) with successful pig islet xenografts. The leukocytes cause rejection of the xenograft.

Plastic adherence (to deplete macrophages), nylon wool adherence (to deplete non-T lymphocytes), or specific antibodies (anti-CD4, anti-CD8, anti-F4/80, anti-B220) are used to deplete the total splenocyte preparations of certain classes of leukocytes. The class-depleted leukocyte preparations are injected into the NOD/scid mice with successful pig islet xenografts to determine which leukocyte class is necessary and sufficient to cause xenograft rejection.

Spleen leukocytes are isolated by conventional methods known in the art from mice (xenograft acceptor of Example 8) that have accepted their pig islet xenografts. These leukocytes are administered to NOC/scid mice with successful pig islet xenografts. The leukocytes do not cause rejection of the xenograft. Combining the appropriate leukocyte-depleted preparation that causes rejection with leukocytes from a xenograft acceptor of Example 8 (50/50 mixture) and administering the mixed cell population to NOD/scid xenograft recipients (adoptive transfer) allows determination of whether so-called suppressor lymphocytes are preventing xenograft rejection in xenograft acceptors.

EXAMPLE 10

This example provides a method of encapsulation of Sertoli cells with islets for transplantation.
Preparation of Islets and Sertoli Cell Isolation Islets are isolated from female Fischer rats and are incubated in CMRL medium for approximately four days prior to usage. Sertoli cells are isolated from weanling male Fischer rats and are incubated for approximately four days to confluency in Petri dishes at 37° C.

After four days of incubation, the islets are counted and groups of 50 islets are transferred to 24 well Petri dishes. Sertoli cells are removed from Petri dishes with Sigma non-enzymatic media. The Sertoli cells are washed and counted.

Three experimental groups are then established as follows: Group 1: 12-well Petri dishes, each well containing 50 islets; Group 2: 12-well Petri dishes, each well containing a total of $1\times10^4$ Sertoli cells; and Group 3: 12-well Petri dishes, each well containing 50 islets, plus $1\times10^4$ Sertoli cells. The Petri dishes are incubated at 37° C. for 24 hours to permit Sertoli cells to attach to islets.
Microencapsulation of Islets and Sertoli Cells Islets, Sertoli cells and islets plus Sertoli cells are encapsulated by suspension in a solution of sodium alginate which is sprayed into a dish of calcium chloride using a droplet forming device according to the method of Lim et al. (1980 Science 210:908–910, the contents of which is incorporated by reference. The droplets are coated with a layer of poly- L-lysine (PLL) with an average size of 20 kDa at a concentration of 0.05% (w/v) and a reaction time of 6 minutes according to the method of Goosen et al. (1985) Biotechnol. Bioeng. 27:146–150, the contents of which is incorporated by reference. An additional outer layer of sodium alginate is added around the capsule according to the method of O'Shea et al. (1984) Biochim. Biophys. Acta 804:133–136, incorporated herein by reference. Alternatively, isolated cells may be encapsulated according to the methodology of Weber et al. U.S. Pat. No. 5,227,298, incorporated herein by reference. Following encapsulation, the cells are divided into treatment groups. Group 1: Free islets, not encapsulated, Group 2: Islets alone, encapsulated, Group 3: Sertoli cells alone, encapsulated, and Group 4: Islets plus Sertoli cells encapsulated. Encapsulated cells are placed in media conventionally selected by the skilled artisan at 37° C.

In Vitro Encapsulation

At specified intervals following encapsulation, i.e., 1, 7, 14, 21 and 30 days respectively, following incubation, functionality of the groups containing islets are examined. Approximately 10 capsules from each of the islet containing groups are stimulated, in tandem, by a buffered medium containing glucose 9 mmol/L, glucose at 16.7 mmol/L, and Forskolin at 10 mM for 30 minutes, in a water bath at 37° C. The perfusate is collected and insulin is assayed using a commercially available kit (e.g., Linco insulin kit). Insulin content of free encapsulated islets and islets encapsulated with Sertoli cells is further examined via an acid-ethanol extract of said capsules and assayed for insulin content using a commercially available kit (e.g. Linco insulin kit).

In Vivo Encapsulation

Female Wistar-Furth rats are made diabetic by means of a single i.v. injection of streptozotocin. A total of 32 diabetic rats are divided into four groups and treated as follows: Group 1, a control group (n=8), will receive an intraperitoneal injection of at least 10 capsules containing Sertoli cells alone; Group 2 (n=8) will receive an intraperitoneal injection of 10 islets/g of free, non-encapsulated islets; Group 3 (n=8) will receive an i.p. injection of 10 islets/g of encapsulated islets alone; Group 4, (n=8) will receive 10 islets/g of co-encapsulated islets plus Sertoli cells. No group will receive any immunosuppression following transplantation. All rats are closely monitored via daily plasma glucose levels for the first week post-transplantation, and then at weekly intervals thereafter.

Rats are considered cured of diabetes if they exhibit a blood glucose level less than or equal to 170 mg/dl with concomitant steady increases in body weight.

EXAMPLE 11

This example describes a method of immortalizing Sertoli cells using a temperature-sensitive mutant of the SV40 virus.

Sertoli cells are isolated from sexually mature (120 days) rats according to the method of Wright et al. (1989) Ann. NY Acad. Sci. 564:173–185. The testes are removed and the tubules are resuspended in DMEM F-12 (DMEM/F12: Life Technologies, Inc., Grand Island, N.Y.) containing 1 mg/ml collagenase (Worthington, Freehold, N.J.), 2mg/ml hyaluronidase (Sigma, St. Louis, Mo.), 0.3 mg/ml DNase (Sigma), and 65 ug/ml soybean trypsin inhibitor (Sigma), and are incubated for 25 min at 32° C. with gentle shaking. The incubation is repeated and the tubules are washed in F12/DMEM and digested in an enzyme solution including 1 mg/ml collagenase/dipase (Boehringer-Mannheim, Indianapolis, Ind.) in lieu of collagenase. The tubules are recovered and further broken up by gentle pipetting with a Pasteur pipette. The digestion mixture is filtered through a nylon mesh to remove clumps of undispersed Sertoli cells. The Sertoli cells are then sedimented at unit gravity yielding a 95% pure population of adult Sertoli cells.

Two 25-cm$^2$ flasks are seeded with Sertoli cells at a density of $5 \times 10^6$ cells per plate. These flasks are incubated with SV40 virus mutant tsA255 for 3 h. The virus-containing medium is removed, and the cells are incubated at 33° C. in F12/DMEM supplemented with 4% fetal bovine serum (FBS). Foci of transformed cells are visible at 6 weeks after infection. Each individual focus is isolated with sterile metal rings, the cells are isolated from the plate with trypsin EDTA, and the cell suspensions are replated in 25-cm$^2$ flasks. Aliquots of cells from each focus are cultured at 33° C. or 40° C. for two days. At the end of this culture period, the cells are collected and total RNA is isolated for Northern blot analysis according to the methodology of Roberts, et al. (1992) Biol. Reprod. 47:92–96, incorporated herein by reference. Sertoli cells are selected for cloning on the basis of the inducible expression of mRNAs encoding Sertoli cell-secreted proteins according to the methods of Roberts, et al. (1995) Biol. Reprod. 53:1446–1453, incorporated herein by reference. Clonal cells are cultured in DMEM/F12 Plus 4% FBS, supplemented with 1% antibiotic-antimycotic. The cells are then seeded and allowed to attach at 33° C. for at least 24 hours. Clonal cells are collected by washing the plates twice with Hanks balanced salt solution followed by a brief incubation with trypsin/EDTA.

What is claimed is:

1. A method of creating an immunologically privileged site in a mammal wherein said method comprises transplanting isolated Sertoli cells obtained from a cell line into a mammal.

2. The method of claim 1 wherein said mammal is a human.

3. The method of claim 1 wherein said Sertoli cells are injected into the renal subcapsular space.

4. The method of claim 1 wherein said Sertoli cells are injected into the subcutaneous facie.

5. The method of claim 1 wherein said Sertoli cells are transplanted at a dosage ranging from $10^5$ to $10^{10}$ cells.

6. The method of claim 5 wherein said Sertoli cells are obtained by the steps comprising:
   a. isolating mammalian Sertoli cells from mammalian tissue;
   b. incubating said isolated mammalian Sertoli cells with a mutagen under conditions sufficient to transform said Sertoli cells;
   c. collecting said transformed Sertoli cells; and
   d. optionally screening transformed Sertoli cells for expression of an appropriate isolate for cloning.

7. The method of claim 1 wherein said Sertoli-cells are human, bovine or porcine.

8. The method of claim 1 wherein said Sertoli cells are obtained by the steps comprising:
   a. isolating mammalian Sertoli cells from mammalian tissue;
   b. incubating said isolated mammalian Sertoli cells with virus producing cells under conditions sufficient to transform said Sertoli cells;
   c. isolating said transformed Sertoli cells from the virus producing cell; and
   d. optionally screening transformed Sertoli cells for expression of an appropriate isolate for cloning.

9. The method of claim 8 wherein said virus producing cells are SV40 or polyoma virus.

10. The method of claim 1 wherein said Sertoli cells are obtained by the steps comprising:
   a. isolating mammalian Sertoli cells from mammalian tissue;
   b. incubating said isolated mammalian Sertoli cells with a mutagen under conditions sufficient to transform said Sertoli cells;
   c. collecting said transformed Sertoli cells; and
   d. optionally screening transformed Sertoli cells for expression of an appropriate isolate for cloning.

11. A method of creating systemic tolerance to subsequent transplants comprising transplanting Sertoli cells prior to said subsequent transplant with a transplant in an amount sufficient to tolerize said mammal.

12. The method of claim 11 wherein said transplants are endocrine cells.

13. The method of claim 11 wherein said Sertoli cells are administered in a dosage ranging from $10^5$ to $10^{10}$ cells.

14. The method of claim 11 wherein endocrine cells are simultaneously transplanted with said Sertoli cells.

15. The method of claim 11 wherein said Sertoli cells are obtained from a cell line.

16. The method of claim 15 wherein said Sertoli cells are obtained by the steps comprising:
   a. isolating mammalian Sertoli cells from mammalian tissue;
   b. incubating said isolated mammalian Sertoli cells with virus producing cells under conditions sufficient to transform said Sertoli cells;
   c. isolating said transformed Sertoli cells from the virus producing cell; and
   d. optionally screening transformed Sertoli cells for expression of an appropriate isolate for cloning.

17. The method of claim 16 wherein said virus producing cells are SV40 or polyoma virus.

18. A method of enhancing the maturation, proliferation and functional capacity of mammalian cells in tissue culture comprising co-culturing said cells with Sertoli cells.

19. The method of claim 18 wherein said Sertoli cells are co-cultured in an amount ranging from $10^5$ to $10^{10}$ cells.

20. The method of claim 18 wherein said Sertoli cells are obtained from a cell line.

21. The method of claim 20 wherein said Sertoli cells are obtained by the steps comprising:
   a. isolating mammalian Sertoli cells from mammalian tissue;
   b. incubating said isolated mammalian Sertoli cells with virus producing cells under conditions sufficient to transform said Sertoli cells;
   c. isolating said transformed Sertoli cells from the virus producing cell; and
   d. optionally screening transformed Sertoli cells for expression of an appropriate isolate for cloning.

22. The method of claim 20 wherein said Sertoli cells are obtained by the steps comprising:
   a. isolating mammalian Sertoli cells from mammalian tissue;
   b. incubating said isolated mammalian Sertoli cells with a mutagen under conditions sufficient to transform said Sertoli cells;
   c. collecting said transformed Sertoli cells; and
   d. optionally screening transformed Sertoli cells for expression of an appropriate isolate for cloning.

23. The method of claim 18 wherein said virus producing cells are SV40 or polyoma virus.

24. The method of claim 18 wherein the mammalian cells and the Sertoli cells are co-localized.

25. The method of claim 18 wherein the mammalian cells and the Sertoli cells are co-encapsulated.

26. A method of enhancing the recovery rate and viability of frozen mammalian cells in tissue culture-comprising co-culturing said cells with Sertoli cells.

27. The method of claim 26 wherein said mammalian cells are endocrine cells or germ cells.

28. A pharmaceutical composition comprising Sertoli cells obtained from a cell line, pancreatic islet of Langerhans cells and a pharmaceutically acceptable carrier.

29. A pharmaceutical composition comprising Sertoli-cells obtained from a cell line and a pharmaceutically acceptable carrier.

30. An article of manufacture comprising a packaging material and Sertoli cells contained within said packaging material, wherein said Sertoli cells are effective for creating an immunologically privileged site in a mammal, and wherein said packaging material contains a label that indicates that said Sertoli cells can be used for creating an immunologically privileged site in a mammal.

31. A pharmaceutical composition comprising Sertoli cells obtained from a cell line, and cells that produce a biological factor and a pharmaceutically acceptable carrier.

32. The composition of claim 31 wherein said biological factor is a hormone.

33. The composition of claim 31 wherein said cells that produce a biological factor are pancreatic islet of Langerhans cells.

34. The composition of claim 31 wherein said cells that produce said biological factor are cells that are transformed by a nucleic acid encoding said biological factor.

35. The composition of claim 31 wherein said Sertoli cells are obtained by the steps comprising:
   a. isolating mammalian Sertoli cells from mammalian tissue;
   b. incubating said isolated mammalian Sertoli cells with virus producing cells under conditions sufficient to transform said Sertoli cells;
   c. isolating said transformed Sertoli cells from the virus producing cell; and
   d. optionally screening transformed Sertoli cells for expression of an appropriate isolate for cloning.

36. The composition of claim 31 wherein said Sertoli cells are obtained by the steps comprising:
   a. isolating mammalian Sertoli cells from mammalian tissue;
   b. incubating said isolated mammalian Sertoli cells with a mutagen under conditions sufficient to transform said Sertoli cells;
   c. collecting said transformed Sertoli cells; and
   d. optionally screening transformed Sertoli cells for expression of an appropriate isolate for cloning.

37. The composition of claim 31 wherein said virus producing cells are SV40 or polyoma virus.

* * * * *

UNITED STATES PATENT AND TRADEMARK OFFICE
CERTIFICATE OF CORRECTION

PATENT NO. : 6,149,907 Page 1 of 1
DATED : November 21, 2000
INVENTOR(S) : H. Selawry It is certified that error appears in the above-identified patent and that said Letters Patent is hereby corrected as shown below:

<u>Column 4,</u>
Line 43, "islet-cells" should read -- islet cells --
Line 52, insert -- The file of this patent contains at least one drawing executed in color as determined by the U.S. Patent and Trademark Office. Copies of this patent with color drawing(s) will be provided by the Patent and Trademark Office upon request and payment of the necessary fees. --

<u>Column 15,</u>
Line 49, "G label" should read -- label --

<u>Column 19,</u>
Line 61, "divider" should read -- divided --

<u>Column 26,</u>
Line 41, "$5X10^6$" should read -- 5X106 --

Signed and Sealed this

Thirteenth Day of August, 2002

*Attest:*

*Attesting Officer*

JAMES E. ROGAN
*Director of the United States Patent and Trademark Office*